(12) United States Patent
Cheng et al.

(10) Patent No.: US 8,119,661 B2
(45) Date of Patent: *Feb. 21, 2012

(54) PIPERIDINE DERIVATIVES AND THEIR USE AS MUSCARINIC RECEPTOR MODULATORS

(75) Inventors: Yun-Xing Cheng, Montreal (CA); Xuehong Luo, Montreal (CA); Vijayaratnam Santhakumar, Montreal (CA); Miroslaw Jerzy Tomaszewski, Montreal (CA)

(73) Assignee: AstraZeneca AB, Sodertalje (SE)

( * ) Notice: Subject to any disclaimer, the term of this patent is extended or adjusted under 35 U.S.C. 154(b) by 648 days.

This patent is subject to a terminal disclaimer.

(21) Appl. No.: 12/205,968

(22) Filed: Sep. 8, 2008

(65) Prior Publication Data

US 2009/0076078 A1    Mar. 19, 2009

Related U.S. Application Data

(60) Provisional application No. 60/971,288, filed on Sep. 11, 2007.

(51) Int. Cl.
*A61K 31/454* (2006.01)
*C07D 403/14* (2006.01)

(52) U.S. Cl. .................. 514/322; 546/187; 546/199

(58) Field of Classification Search .................. 514/322; 546/187, 199
See application file for complete search history.

(56) References Cited

U.S. PATENT DOCUMENTS

| | | | |
|---|---|---|---|
| 5,665,719 A | 9/1997 | Bock et al. | |
| 5,756,497 A | 5/1998 | Bell et al. | |
| 5,756,508 A | 5/1998 | Thompson et al. | |
| 6,172,067 B1 | 1/2001 | Ito et al. | |
| 6,258,811 B1 | 7/2001 | Yamauchi et al. | |
| 6,812,226 B2 | 11/2004 | Baxter et al. | |
| 7,956,069 B2 * | 6/2011 | Cheng et al. | 514/322 |
| 2007/0287695 A1 * | 12/2007 | Cheng et al. | 514/210.21 |

FOREIGN PATENT DOCUMENTS

| | | |
|---|---|---|
| EP | 0029707 B1 | 2/1984 |
| EP | 0608858 A1 | 1/1994 |
| EP | 1386920 A1 | 2/2004 |
| EP | 1221443 B1 | 9/2004 |
| EP | 1790637 A1 | 5/2007 |
| JP | 2000323278 | 11/2000 |
| JP | 2002302675 | 10/2002 |
| WO | 9502405 | 1/1995 |
| WO | 9613262 | 5/1996 |
| WO | 9716192 | 5/1997 |
| WO | 9811128 | 3/1998 |
| WO | 9936421 | 2/1999 |
| WO | 9929686 | 6/1999 |
| WO | 9932481 | 7/1999 |
| WO | 0144213 | 6/2001 |
| WO | 0214315 | 2/2002 |
| WO | 02085357 | 10/2002 |
| WO | 02085361 | 10/2002 |
| WO | 03037890 | 5/2003 |
| WO | 03088967 | 10/2003 |
| WO | 03105781 | 12/2003 |
| WO | 2004069828 | 8/2004 |
| WO | 2004089942 | 10/2004 |
| WO | 2004099159 | 11/2004 |
| WO | 2005042517 | 5/2005 |
| WO | 2005060711 | 7/2005 |
| WO | 2005060947 | 7/2005 |
| WO | 2005117883 | 12/2005 |
| WO | 2006037052 | 4/2006 |
| WO | 2006038594 | 4/2006 |
| WO | 2006130469 | 12/2006 |
| WO | 2007036711 | 4/2007 |
| WO | 2007142583 | 12/2007 |

OTHER PUBLICATIONS

Bartolini A. et al, Role of muscarinic receptor subtypes in central antinociception. Br. J. Pharmacol. 105:77-82, 1992.

Capone F et al, "Oxotremorine-induced modifications of the behavioral and neuroendocrine responses to formalin pain in male rats", Brain Res. 830:292-300, 1999.

Caulfield, M.P., "Muscarinic Receptors-Characterization, Coupling, and Function," Pharmacol. Ther., 58, pp. 319-379 (1993).

Caulfield, M.P. et al, "International Union of Pharmacology. XVII. Classification of Muscarinic Acetylcholine Receptors," Pharmacol. Rev., 50, pp. 279-290 (1998).

DeLapp, N. et al, "Therapeutic Opportunities for Muscarinic Receptors in the Central Nervous System," J. Med. Chem., 43(23), pp. 4333-4353 (2000).

Hulme, E.C. et al, "Muscarinic Receptor Subtypes," Ann. Rev. Pharmacol. Toxicol., 30, pp. 633-673 (1990).

Hwang, J.-H. et al, "The antiallodynic effects of intrathecal cholinesterase inhibitors in a rat model of neuropathic pain", Anesthesiology 90:492-494, 1999.

(Continued)

*Primary Examiner* — Susannah Chung

(57) ABSTRACT

Compounds of Formula I, or pharmaceutically acceptable salts thereof:

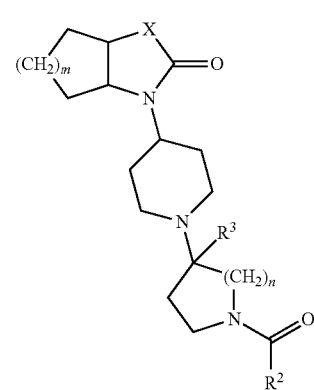

wherein $R^2$, $R^3$, X, m and n are as defined in the specification as well as salts and pharmaceutical compositions including the compounds are prepared. They are useful in therapy, in particular in the management of pain.

1 Claim, No Drawings

OTHER PUBLICATIONS

Lee, E.J. et al, "Intrathecal carbachol and clonidine produce a synergistic antiallodynic effect in rats with a nerve ligation injury", Can J Anaesth 49:178-84, 2002.

Obase, H et al: "New Antihypertensive Agents. III. Synthesis and Antihypertensive Activity of Some Arylalkyl Piperidines Carrying a Heterocycle at the 4-Position", Chemical and Pharmaceutical Bulletin, Pharmaceutical Society of Japan, Tokyo, JP, vol. 31, No. 9, 1983, pp. 3186-3197, XP002149262 ISSN: 0009-2363.

English abstract for JP 2000-323278, Date: Nov. 24, 2000.
English abstract for JP 2002-302675, Date: Oct. 18, 2002.
English abstract for EP 0608858, Date: Jan. 26, 1994.
English abstract for WO 9811128, Date: Mar. 19, 1998.
English abstract for WO 2004069828, Date: Aug. 19, 2004.
English abstract for WO 2006038594, Date: Apr. 13, 2006.
International Search Report issued for PCT/SE2007/000554 on Sep. 20, 2007.
Cecil Textbook of Medicine, 20th Edition, vol. 2, 1996, pp. 1992-1996.
PubMed Abstract 12621313; J. Cereb Blood Flow Metab., Mar. 2003, 23(3), 381-4.
PubMed Abstract 12910626; J. Soc. Biol., 2003, 197(2), 113-22.
PubMed Abstract 14511112; J. Neurochem, Oct. 2003, 87(2), 344-52.
PubMed Abstract 14561158; Curr. Drug Targets Inflamm Allergy, Sep. 2003, 2(3), 232-41.

Ferrari et al., "Extracellular ATP Triggers IL-1 Release by Activating the Purinergic P2Z Receptor of Human Macrophages," Journal of Immunology, vol. 159(3), 1997, pp. 1451-1458.

Ferrari et al., "Purinergic Modulation of Interleukin-1 Release from Microglial Cells Stimulated with Bacterial Endotoxin," J. Exp. Med., vol. 185(3), 1997, pp. 579-582.

Henderson et al., "Inhibition of Interleukin-1-Induced Synovitis and Articular Cartilage Proteoglycan Loss in the Rabbit Knee by Recombinant Human Interleukin-1 Receptor Antagonist," Cytokine, vol. 3(3), 1991, pp. 246-249.

Kadota et al., "Significance of IL-1 and IL-1 Receptor Antagonist (IL-1Ra) in Bronchoalveolar Lavage Fluid (BALF) in Patients with Diffuse Panbronchiolitis (DPB)," Clin. Exp. Immunol., vol. 103, 1996, pp. 461-466.

Otterness et al., "Possible Role of IL-1 in Arthritis: Effects of Prostaglandins in the Regulation of IL-1 Synthesis and Actions," Joint Destruction in Arthritis and Osteoarthritis, Agents and Actions Supplements, vol. 39, 1993, pp. 109-120.

Sakito et al., "Interleukin 1, Tumor Necrosis Factor Alpha, and Interleukin 8 in Bronchoalveolar Lavage Fluid of Patients with Diffuse Panbronchiolitis: A Potential Mechanism of Macrolide Therapy," Respiration, vol. 63, 1996, pp. 42-48.

Yu et al., "Inhibition of IL-1 Release from Human Monocytes and Suppression of Streptococcal Cell Wall and Adjuvant-induced Arthritis in Rats by an Extract of Tripterygium Wilfordii Hook," General Pharmacology, vol. 25(6), 1994, pp. 1115-1122.

* cited by examiner

PIPERIDINE DERIVATIVES AND THEIR USE AS MUSCARINIC RECEPTOR MODULATORS

CROSS-REFERENCE TO RELATED APPLICATIONS

This application claims the benefit under 35 U.S.C. §119(e) to Application No. 60/971,288 filed on Sep. 11, 2007.

BACKGROUND OF THE INVENTION

1. Field of the Invention

The present invention relates to agonists of muscarinic receptors. The present invention also provides compositions comprising such agonists, and methods therewith for treating muscarinic receptor mediated diseases. Particularly, the present invention is related to compounds that may be effective in treating pain, Alzheimer's disease, and/or schizophrenia.

2. Discussion of Relevant Technology

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs) and show a remarkably high degree of homology across species and receptor subtype. These M1-M5 muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," J. Med. Chem., 43 (23), pp. 4333-4353 (2000); Hulme, E. C. et al., "Muscarinic Receptor Subtypes," Ann. Rev. Pharmacol. Toxicol., 30, pp. 633-673 (1990); Caulfield, M. P. et al., "Muscarinic Receptors-Characterization, Coupling, and Function," Pharmacol. Ther., 58, pp. 319-379 (1993); Caulfield, M. P. et al., International Union of Pharmacology. XVII. Classification of Muscarinic Acetylcholine Receptors," Pharmacol. Rev., 50, pp. 279-290 (1998).

The Muscarinic family of receptors is the target of a large number of pharmacological agents used for various diseases, including leading drugs for COPD, asthma, urinary incontinence, glaucoma, schizophrenia, Alzheimer's (AchE inhibitors), and Pain.

For example, direct acting muscarinic receptor agonists have been shown to be antinociceptive in a variety of animal models of acute pain (Bartolini A., Ghelardini C., Fantetti L., Malcangio M., Malmberg-Aiello P., Giotti A. Role of muscarinic receptor subtypes in central antinociception. Br. J. Pharmacol. 105:77-82, 1992; Capone F., Aloisi A. M., Carli G., Sacerdote P., Pavone F. Oxotremorine-induced modifications of the behavioral and neuroendocrine responses to formalin pain in male rats. Brain Res. 830:292-300, 1999).

A few studies have examined the role of muscarinic receptor activation in chronic or neuropathic pain states. In these studies, the direct and indirect elevation of cholinergic tone was shown to ameliorate tactile allodynia after intrathecal administration in a spinal ligation model of neuropathic pain in rats and these effects again were reversed by muscarinic antagonists (Hwang J.-H., Hwang K.-S., Leem J.-K., Park P.-H., Han S.-M., Lee D.-M. The antiallodynic effects of intrathecal cholinesterase inhibitors in a rat model of neuropathic pain. Anesthesiology 90:492-494, 1999; Lee E. J., Sim J. Y, Park J. Y., Hwang J. H., Park P. H., Han S. M. Intrathecal carbachol and clonidine produce a synergistic antiallodynic effect in rats with a nerve ligation injury. Can J Anaesth 49:178-84, 2002). Thus, direct or indirect activation of muscarinic receptors has been shown to elicit both acute analgesic activity and to ameliorate neuropathic pain. Muscarinic agonists and ACHE-Is are not widely used clinically owing to their propensity to induced a plethora of adverse events when administered to humans. The undesirable side effects include excessive salivation and sweating, enhanced gastrointestinal motility, and bradycardia among other adverse events. These side effects are associated with the ubiquitous expression of the muscarinic family of receptors throughout the body.

DESCRIPTION OF THE EMBODIMENTS

To date, five subtypes of muscarinic receptors (M1-M5) have been cloned and sequenced from a variety of species, with differential distributions in the body.

Therefore, it was desirable to provide molecules would permit selective modulation, for example, of muscarinic receptors controlling central nervous function without also activating muscarinic receptors controlling cardiac, gastrointestinal or glandular functions.

There is also a need for methods for treating muscarinic receptor-mediated diseases.

There is also a need for modulators of muscarinic receptors that are selective as to subtypes M1-M5.

The term "$C_{m-n}$" or "$C_{m-n}$ group" refers to any group having m to n carbon atoms.

The term "alkyl" refers to a saturated monovalent straight or branched chain hydrocarbon radical comprising 1 to about 12 carbon atoms. Illustrative examples of alkyls include, but are not limited to, $C_{1-6}$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl can be unsubstituted or substituted with one or two suitable substituents.

The term "alkenyl" refers to a monovalent straight or branched chain hydrocarbon radical having at least one carbon-carbon double bond and comprising at least 2 up to about 12 carbon atoms. The double bond of an alkenyl can be unconjugated or conjugated to another unsaturated group. Suitable alkenyl groups include, but are not limited to $C_{2-6}$alkenyl groups, such as vinyl, allyl, butenyl, pentenyl, hexenyl, butadienyl, pentadienyl, hexadienyl, 2-ethyl hexenyl, 2-propyl-2-butenyl, 4-(2-methyl-3-butene)-pentenyl. An alkenyl can be unsubstituted or substituted with one or two suitable substituents.

The term "cycloalkyl" refers to a saturated monovalent ring-containing hydrocarbon radical comprising at least 3 up to about 12 carbon atoms. Examples of cycloalkyls include, but are not limited to, $C_{3-7}$cycloalkyl groups, such as cyclopropyl, cyclobutyl, cyclopentyl, cyclohexyl, and cycloheptyl, and saturated cyclic and bicyclic terpenes. A cycloalkyl can be unsubstituted or substituted by one or two suitable substituents. Preferably, the cycloalkyl is a monocyclic ring or bicyclic ring.

The term "aryl" refers to a monovalent hydrocarbon radical having one or more polyunsaturated carbon rings having aromatic character, (e.g., 4n+2 delocalized electrons) and comprising 5 up to about 14 carbon atoms.

The term "heterocycle" refers to a ring-containing structure or molecule having one or more multivalent heteroatoms, independently selected from N, O, P and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heterocyclyl" refers a monovalent radical derived from a heterocycle by removing one hydrogen therefrom.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "heteroaryl" refers to a heterocyclyl having aromatic character.

The term "heterocycloalkyl" refers to a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 6 carbon atoms and form 1 to 3 heteroatoms, referred to herein as $C_{3-6}$heterocycloalkyl.

The term "six-membered" refers to a group having a ring that contains six ring atoms.

The term "five-membered" refers to a group having a ring that contains five ring atoms.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

The term "alkoxy" refers to radicals of the general formula —O—R, wherein R is selected from a hydrocarbon radical. Exemplary alkoxy includes methoxy, ethoxy, propoxy, isopropoxy, butoxy, t-butoxy, isobutoxy, cyclopropylmethoxy, allyloxy, and propargyloxy.

Halogen includes fluorine, chlorine, bromine and iodine.

"RT" or "rt" means room temperature.

"Preparative LC/MS (high pH)" means high performance liquid chromatography with mass detection in preparative scale. Conditions used—Column: Waters X-Bridge Prep C18 OBD, 30×50 mm, 5 um particle size, Mobile phase: A=Water 10 mM $NH_4HCO_3$ (pH 10) and B: MeCN.

"Preparative LC/MS (Low pH)" means high performance liquid chromatography with mass detection in preparative scale. Conditions used—Column: Waters Synergy Polar Prep C18 OBD, 30×50 mm, 4 um particle size, Mobile phase: A=0.05% TFA in Water and B: MeCN.

"HATU" means O-(7-Azabenzotriazol-1-yl)-N,N,N',N'-tetramethyluronium hexafluorophosphate.

"DCC" means N,N'-Dicyclohexylcarbodiimide.

"EDC" means 1-Ethyl-3-(3-dimethylaminopropyl)carbodiimidehydrochloride.

"CDI" means 1,1'-Carbonyldiimidazole.

"DIPEA" means Diisopropylethylamine.

The compounds described in this application may be named with the IUPAC naming software Lexichem (version 1.4/version 1.6)

In one aspect, an embodiment of the invention provides a compound of Formula I, a pharmaceutically acceptable salt thereof, diastereomer, enantiomer, or mixture thereof:

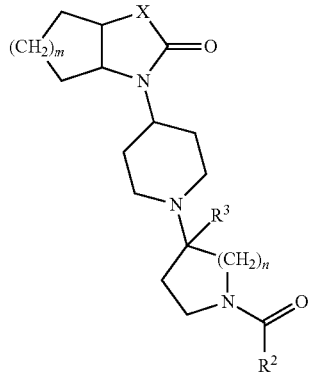

wherein

R² is selected from hydrogen, $C_{3-7}$cycloalkyl, $C_{1-7}$alkyl, $C_{2-6}$alkenyl, $C_{2-6}$alkynyl, $C_{1-7}$alkoxy, $C_{2-6}$alkenyloxy, $C_{2-6}$alkynyloxy, $C_{1-6}$alkylamino, di-$C_{1-6}$alkylamino, $C_{3-7}$heterocycloalkyloxy, $C_{3-7}$heterocycloalkyl, $C_{6-10}$aryl-$C_{1-3}$alkoxy, $C_{6-10}$aryl-$C_{1-3}$alkyl, $C_{3-9}$heteroaryl-$C_{1-3}$alkoxy, $C_{3-9}$heteroaryl-$C_{1-3}$alkyl, $C_{3-7}$heterocycloalkyl-$C_{1-3}$alkoxy, $C_{3-7}$heterocycloalkyl-$C_{1-3}$alkyl, $C_{3-7}$cycloalkyloxy, $C_{3-7}$cycloalkyl-$C_{1-3}$alkyl, and $C_{3-7}$cycloalkyl-$C_{1-3}$alkoxy, wherein said $C_{3-7}$cycloalkyl, $C_{1-7}$alkyl, $C_{2-6}$alkenyl, $C_{2-6}$alkynyl, $C_{1-7}$alkoxy, $C_{2-6}$alkenyloxy, $C_{2-6}$alkynyloxy, $C_{1-6}$alkylamino, di-$C_{1-6}$alkylamino, $C_{3-7}$heterocycloalkyloxy, $C_{3-7}$heterocycloalkyl, $C_{6-10}$aryl-$C_{1-3}$alkoxy, $C_{6-10}$aryl-$C_{1-3}$alkyl, $C_{3-9}$heteroaryl-$C_{1-3}$alkoxy, $C_{3-9}$heteroaryl-$C_{1-3}$alkyl, $C_{3-7}$heterocycloalkyl-$C_{1-3}$alkoxy, $C_{3-7}$heterocycloalkyl-$C_{1-3}$alkyl, $C_{3-7}$cycloalkyloxy, $C_{3-7}$cycloalkyl-$C_{1-3}$alkyl, and $C_{3-7}$cycloalkyl-$C_{1-3}$alkoxy are optionally substituted with one or more group selected from phenyl, $C_{3-6}$cycloalkyl, $C_{2-5}$heterocycloalkyl, $C_{3-5}$heteroaryl, —CN, —SR, —OR, —O(CH₂)$_p$—OR, R, —C(=O)—R, —CO₂R, —SO₂R, —SO₂NRR', halogen, —NO₂, —NRR', —(CH₂)$_p$NRR', and —C(=O)—NRR';

R³ is selected from $C_{1-6}$alkyl and halogenated $C_{1-6}$alkyl;

p is 1, 2, 3 or 4; m and n are independently 1, 2, 3 or 4;

X is independently selected from NH, N—R, CH₂, CHR, and CRR'; and each R, R' is independently hydrogen, $C_{1-6}$alkyl, $C_{2-6}$alkenyl or halogenated $C_{1-6}$alkyl, with a proviso that said compound is not selected from
ethyl 4-[4-[(3aS,7aS)-2-oxo-3a,4,5,6,7,7a-hexahydro-3H-benzoimidazol-1-yl]-1-piperidyl]-4-ethyl-piperidine-1-carboxylate;
(3aS,7aS)-1-[1-[1-(cyclopropanecarbonyl)-4-propyl-4-piperidyl]-4-piperidyl]-3a,4,5,6,7,7a-hexahydro-3H-benzoimidazol-2-one;
tert-butyl 4-[4-[(3aS,7aS)-2-oxo-3a,4,5,6,7,7a-hexahydro-3H-benzoimidazol-1-yl]-1-piperidyl]-4-methyl-piperidine-1-carboxylate;
tert-butyl 4-[4-[(3aR,7aR)-2-oxo-3a,4,5,6,7,7a-hexahydro-3H-benzoimidazol-1-yl]-1-piperidyl]-4-methyl-piperidine-1-carboxylate;
propan-2-yl 4-[4-[(3aS,7aS)-2-oxo-3a,4,5,6,7,7a-hexahydro-3H-benzoimidazol-1-yl]-1-piperidyl]-4-ethyl-piperidine-1-carboxylate;
propan-2-yl 4-[4-[(3aS,7aS)-2-oxo-3a,4,5,6,7,7a-hexahydro-3H-benzoimidazol-1-yl]-1-piperidyl]-4-propyl-piperidine-1-carboxylate; and
ethyl 4-[4-[(3aS,7aS)-2-oxo-3a,4,5,6,7,7a-hexahydro-3H-benzoimidazol-1-yl]-1-piperidyl]-4-propyl-piperidine-1-carboxylate.

In another embodiment, R² is selected from $C_{1-3}$alkoxy, $C_{1-6}$alkyl, $C_{3-6}$alkynyloxyl, $C_{3-6}$cycloalkyl, halogenated $C_{1-6}$alkyl, and halogenated $C_{3-6}$cycloalkyl.

In another embodiment, R² is ethoxy and isopropyloxy.

In a further embodiment, X is selected from NH and CH₂.

In another embodiment, R² is selected from methyl, ethyl, n-propyl, isopropyl, n-butyl, isobutyl, tert-butyl, propynyloxy, butynyloxy, 4-heptyl, 2-methyl-1-propyl, benzyl, dihydrobenzofuranyl, 2-oxopyrrolidinyl-ethyl, methoxy, ethoxy, isopropoxy, propoxy, benzyloxy, isopropenoxy, isobutoxy, $C_{3-6}$cycloalkoxy, cyclopropyl, cyclobutyl, cyclopentyl, cyclohexyl, pyrrolidinyl, piperidinyl, azetidinyl, methylamino, and ethylamino, which are optionally substituted by one or more groups selected from amino, halogen, phenyl, morpholinyl, CF₃, —C(=O)—$C_{1-6}$alkyl, $C_{3-6}$cycloalkyl, $C_{1-6}$alkyl, hydroxy, $C_{1-6}$alkoxy and —CN.

In another embodiment, R³ is selected from methyl, fluoromethyl, difluoromethyl, and trifluoromethyl.

In a particular embodiment, R³ is methyl.

In a further embodiment, n is 1.

In another embodiment, n is 2.

In another embodiment, m is 2.

In a further embodiment, X is selected from NH and N—R, wherein R is $C_{2-3}$alkenyl or $C_{1-3}$alkyl.

In another embodiment, X is NH.

In another embodiment, X is CH₂.

In a further embodiment, the invention provides a compound selected from
ethyl 4-[4-[(3aS,7aS)-2-oxo-3a,4,5,6,7,7a-hexahydro-3H-benzoimidazol-1-yl]-1-piperidyl]-4-methyl-piperidine-1-carboxylate;
propan-2-yl 4-[4-[(3aS,7aS)-2-oxo-3a,4,5,6,7,7a-hexahydro-3H-benzoimidazol-1-yl]-1-piperidyl]-4-methyl-piperidine-1-carboxylate;
(3aS,7aS)-1-[1-[1-(cyclopropanecarbonyl)-4-methyl-4-piperidyl]-4-piperidyl]-3a,4,5,6,7,7a-hexahydro-3H-benzoimidazol-2-one;
ethyl 4-[4-[(3aR,7aR)-2-oxo-3a,4,5,6,7,7a-hexahydro-3H-benzoimidazol-1-yl]-1-piperidyl]-4-methyl-piperidine-1-carboxylate;
propan-2-yl 4-[4-[(3aR,7aR)-2-oxo-3a,4,5,6,7,7a-hexahydro-3H-benzoimidazol-1-yl]-1-piperidyl]-4-methyl-piperidine-1-carboxylate;
(3aR,7aR)-1-[1-[1-(cyclopropanecarbonyl)-4-methyl-4-piperidyl]-4-piperidyl]-3a,4,5,6,7,7a-hexahydro-3H-benzoimidazol-2-one;
ethyl 3-[4-[(3aS,7aS)-2-oxo-3a,4,5,6,7,7a-hexahydro-3H-benzoimidazol-1-yl]-1-piperidyl]-3-methyl-pyrrolidine-1-carboxylate;
2-fluoroethyl 3-[4-[(3aS,7aS)-2-oxo-3a,4,5,6,7,7a-hexahydro-3H-benzoimidazol-1-yl]-1-piperidyl]-3-methyl-pyrrolidine-1-carboxylate;
prop-2-ynyl 3-[4-[(3aS,7aS)-2-oxo-3a,4,5,6,7,7a-hexahydro-3H-benzoimidazol-1-yl]-1-piperidyl]-3-methyl-pyrrolidine-1-carboxylate;
methyl 3-[4-[(3aS,7aS)-2-oxo-3a,4,5,6,7,7a-hexahydro-3H-benzoimidazol-1-yl]-1-piperidyl]-3-methyl-pyrrolidine-1-carboxylate;
ethyl 3-[4-[(3aR,7aR)-2-oxo-3a,4,5,6,7,7a-hexahydro-3H-benzoimidazol-1-yl]-1-piperidyl]-3-methyl-pyrrolidine-1-carboxylate;
ethyl 4-[4-[(cis)-2-oxo-3a,4,5,6,7,7a-hexahydro-3H-benzoimidazol-1-yl]-1-piperidyl]-4-methyl-piperidine-1-carboxylate;
propan-2-yl 4-[4-[(cis)-2-oxo-3a,4,5,6,7,7a-hexahydro-3H-benzoimidazol-1-yl]-1-piperidyl]-4-methyl-piperidine-1-carboxylate;

propan-2-yl 4-[4-[(3aR,7aS)-2-oxo-3a,4,5,6,7,7a-hexahydro-3H-indol-1-yl]-1-piperidyl]-4-methyl-piperidine-1-carboxylate;

(3aR,7aS)-1-[1-[1-(cyclopropanecarbonyl)-4-methyl-4-piperidyl]-4-piperidyl]-3a,4,5,6,7,7a-hexahydro-3H-indol-2-one;

but-2-ynyl 4-[4-[(3aS,7aS)-2-oxo-3a,4,5,6,7,7a-hexahydro-3H-benzimidazol-1-yl]-1-piperidyl]-4-methyl-piperidine-1-carboxylate;

prop-2-ynyl 4-[4-[(3aS,7aS)-2-oxo-3a,4,5,6,7,7a-hexahydro-3H-benzimidazol-1-yl]-1-piperidyl]-4-methyl-piperidine-1-carboxylate;

(3aS,7aS)-3-[1-(4-methyl-1-propanoyl-4-piperidyl)-4-piperidyl]-3a,4,5,6,7,7a-hexahydro-1H-benzimidazol-2-one;

Diastereomer 1 of but-2-ynyl 3-[4-[(3aS,7aS)-2-oxo-3a,4,5,6,7,7a-hexahydro-3H-benzimidazol-1-yl]-piperidyl]-3-methyl-pyrrolidine-1-carboxylate;

Diastereomer 2 of but-2-ynyl 3-[4-[(3aS,7aS)-2-oxo-3a,4,5,6,7,7a-hexahydro-3H-benzimidazol-1-yl]-1-piperidyl]-3-methyl-pyrrolidine-1-carboxylate;

Diastereomer 1 of ethyl 3-[4-[(3aS,7aS)-2-oxo-3a,4,5,6,7,7a-hexahydro-3H-benzimidazol-1-yl]-1-piperidyl]-3-methyl-pyrrolidine-1-carboxylate;

Diastereomer 2 of ethyl 3-[4-[(3aS,7aS)-2-oxo-3a,4,5,6,7,7a-hexahydro-3H-benzimidazol-1-yl]-1-piperidyl]-3-methyl-pyrrolidine-1-carboxylate;

ethyl 3-[4-[(3aS,7aR)-2-oxo-3a,4,5,6,7,7a-hexahydro-3H-indol-1-yl]-1-piperidyl]-3-methyl-pyrrolidine-1-carboxylate;

enantiomers thereof, diastereomers thereof, pharmaceutically acceptable salts thereof and mixtures thereof.

In another embodiment, the invention provides propan-2-yl 4-[4-[(3aS,7aS)-2-oxo-3a,4,5,6,7,7a-hexahydro-3H-benzoimidazol-1-yl]-1-piperidyl]-4-methyl-piperidine-1-carboxylate or a pharmaceutically acceptable salt thereof.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be appreciated that certain compounds of the present invention may exist as geometrical isomers, for example E and Z isomers of alkenes. The present invention includes any geometrical isomer of a compound of Formula I. It will further be understood that the present invention encompasses tautomers of the compounds of the Formula I.

It will also be understood that certain compounds of the present invention may exist in solvated, for example hydrated, as well as unsolvated forms. It will further be understood that the present invention encompasses all such solvated forms of the compounds of the Formula I.

Within the scope of the invention are also salts of the compounds of the Formula I. Generally, pharmaceutically acceptable salts of compounds of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of Formula I above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

We have now found that the compounds of the invention have activity as pharmaceuticals, in particular as agonists of M1 receptors. More particularly, the compounds of the invention exhibit selective activity as agonist of the M1 receptors and are useful in therapy, especially for relief of various pain conditions such as chronic pain, neuropathic pain, acute pain, cancer pain, pain caused by rheumatoid arthritis, migraine, visceral pain etc. This list should however not be interpreted as exhaustive. Additionally, compounds of the present invention are useful in other disease states in which dysfunction of M1 receptors is present or implicated. Furthermore, the compounds of the invention may be used to treat cancer, multiple sclerosis, Parkinson's disease, Huntington's chorea, schizophrenia, Alzheimer's disease, anxiety disorders, depression, obesity, gastrointestinal disorders and cardiovascular disorders.

In a particular embodiment, the compounds may be used to treat schizophrenia or Alzheimer's disease.

In another embodiment, the compounds may be used to treat pain.

In another particular embodiment, the compounds may be used to treat neuropathic pain.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of M1 receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhea, depression, anxiety and stress-related disorders such as post-traumatic stress disorders, panic disorder, generalized anxiety disorder, social phobia, and obsessive compulsive disorder, urinary incontinence, premature ejaculation, various mental illnesses, cough, lung oedema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following miocardial infarction, obesity, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Also within the scope of the invention is the use of any of the compounds according to the Formula I above, for the manufacture of a medicament for the treatment of any of the conditions discussed above.

A further aspect of the invention is a method for the treatment of a subject suffering from any of the conditions discussed above, whereby an effective amount of a compound according to the Formula I above, is administered to a patient in need of such treatment.

Thus, the invention provides a compound of Formula I or pharmaceutically acceptable salt or solvate thereof, as hereinbefore defined for use in therapy.

In a further aspect, the present invention provides the use of a compound of Formula I or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

The compounds of the present invention are useful in therapy, especially for the therapy of various pain conditions including, but not limited to: acute pain, chronic pain, neuropathic pain, back pain, cancer pain, and visceral pain. In a particular embodiment, the compounds are useful in therapy for neuropathic pain. In an even more particular embodiment, the compounds are useful in therapy for chronic neuropathic pain.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, transdermally, intracerebroventricularly and by injection into the joints.

In one embodiment of the invention, the route of administration may be oral, intravenous or intramuscular.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (percent by weight), more preferably from 0.10 to 50% w, of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

Within the scope of the invention is the use of any compound of Formula I as defined above for the manufacture of a medicament.

Also within the scope of the invention is the use of any compound of Formula I for the manufacture of a medicament for the therapy of pain.

Additionally provided is the use of any compound according to Formula I for the manufacture of a medicament for the therapy of various pain conditions including, but not limited to: acute pain, chronic pain, neuropathic pain, back pain, cancer pain, and visceral pain.

A further aspect of the invention is a method for therapy of a subject suffering from any of the conditions discussed above, whereby an effective amount of a compound according to the Formula I above, is administered to a patient in need of such therapy.

Additionally, there is provided a pharmaceutical composition comprising a compound of Formula I or a pharmaceutically acceptable salt thereof, in association with a pharmaceutically acceptable carrier.

Particularly, there is provided a pharmaceutical composition comprising a compound of Formula I or a pharmaceutically acceptable salt thereof, in association with a pharmaceutically acceptable carrier for therapy, more particularly for therapy of pain.

Further, there is provided a pharmaceutical composition comprising a compound of Formula I or a pharmaceutically acceptable salt thereof, in association with a pharmaceutically acceptable carrier use in any of the conditions discussed above.

In a further embodiment, a compound of the present invention, or a pharmaceutical composition or formulation comprising a compound of the present invention may be administered concurrently, simultaneously, sequentially or separately with one or more pharmaceutically active compound(s) selected from the following:

(i) antidepressants such as amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robalzotan, sertraline, sibutramine, thionisoxetine, tranylcypromaine, trazodone, trimipramine, venlafaxine and equivalents and pharmaceutically active isomer(s) and metabolite(s) thereof;

(ii) atypical antipsychotics including for example quetiapine and pharmaceutically active isomer(s) and metabolite(s) thereof; amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, lithium, loxapine, mesoridazine, olanzapine, paliperidone, perlapine, perphenazine, phenothiazine, phenylbutlypiperidine, pimozide, prochlorperazine, risperidone, quetiapine, sertindole, sulpiride, suproclone, suriclone, thioridazine, trifluoperazine, trimetozine, valproate, valproic acid, zopiclone, zotepine, ziprasidone and equivalents thereof;

(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutlypiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof;

(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof;

(v) anticonvulsants including, for example, carbamazepine, valproate, lamotrogine, gabapentin and equivalents and pharmaceutically active isomer(s) and metabolite(s) thereof;

(vi) Alzheimer's therapies including, for example, donepezil, memantine, tacrine and equivalents and pharmaceutically active isomer(s) and metabolite(s) thereof;

(vii) Parkinson's therapies including, for example, deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof;

(viii) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof;

(ix) stroke therapies including, for example, abciximab, activase, NXY-059, citicoline, crobenetine, desmoteplase, repinotan, traxoprodil and equivalents and pharmaceutically active isomer(s) and metabolite(s) thereof;

(x) over active bladder urinary incontinence therapies including, for example, darafenacin, falvoxate, oxybutynin, propiverine, robalzotan, solifenacin, tolterodine and equivalents and pharmaceutically active isomer(s) and metabolite(s) thereof;

(xi) neuropathic pain therapies including, for example, gabapentin, lidoderm, pregablin and equivalents and pharmaceutically active isomer(s) and metabolite(s) thereof;

(xii) nociceptive pain therapies such as celecoxib, etoricoxib, lumiracoxib, rofecoxib, valdecoxib, diclofenac, loxoprofen, naproxen, paracetamol and equivalents and pharmaceutically active isomer(s) and metabolite(s) thereof;

(xiii) insomnia therapies including, for example, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, zolpidem and equivalents and pharmaceutically active isomer(s) and metabolite(s) thereof; and (xiv) mood stabilizers including, for example, carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combinations employ the compounds of this invention within the dosage range described herein and the other pharmaceutically active compound or compounds within approved dosage ranges and/or the dosage described in the publication reference.

In an even further embodiment, a compound of the present invention, or a pharmaceutical composition or formulation comprising a compound of the present invention may be administered concurrently, simultaneously, sequentially or separately with one or more pharmaceutically active compound(s) selected from buprenorphine; dezocine; diacetylmorphine; fentanyl; levomethadyl acetate; meptazinol; morphine; oxycodone; oxymorphone; remifentanil; sufentanil; and tramadol.

In a particular embodiment, it may be particularly effective to administrate a combination containing a compound of the invention and a second active compound selected from buprenorphine; dezocine; diacetylmorphine; fentanyl; levomethadyl acetate; meptazinol; morphine; oxycodone; oxymorphone; remifentanil; sufentanil; and tramadol to treat chronic nociceptive pain. The efficacy of this therapy may be demonstrated using a rat SNL heat hyperalgesia assay described below.

In a further aspect, the present invention provides a method of preparing the compounds of the present invention.

In one embodiment, the invention provides a process for preparing a compound of Formula I, comprising:

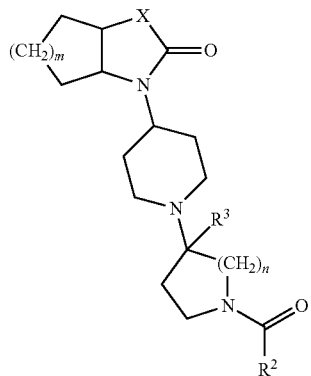

I reacting a compound of Formula II with a compound of Q-C(=O)—R²,

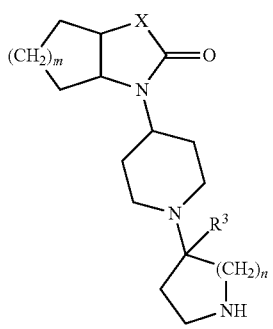

II wherein R², R³, m, n and X are defined above; and Q is a halogen or OH.

Optionally, the step of reacting a compound of formula II with a compound of Q-C(=O)—R², is carried out in the presence of a base, such as diisopropylethylamine, triethylamine or equivalence thereof. When Q is OH, the step of reacting a compound of formula II with a compound of Q-C(=O)—R², is carried out in the presence of a coupling reagent, such as HATU, DCC, EDC or equivalence and a base, such as diisopropylethylamine, triethylamine or equivalence thereof.

In a further embodiment, the present invention provides an intermediate of formula II, a pharmaceutically acceptable salt thereof, diastereomer, enantiomer, or mixture thereof:

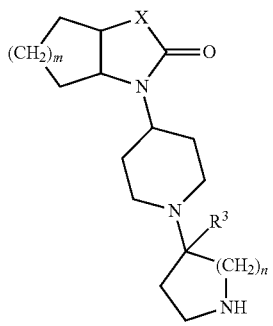

II wherein
n, m, X and R³ are defined as above.

In another embodiment, the present invention provides a process for preparing a compound of Formula III, comprising:

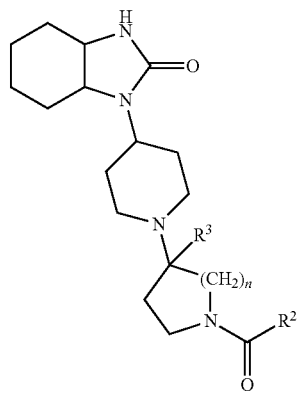

III a) reacting a compound of Formula IV with cyclohexane-1,2-diamine to form a compound of formula V,

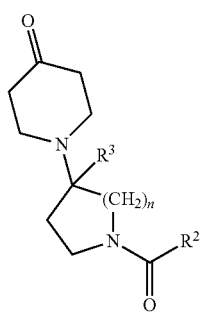

IV b) reacting the compound of formula V with a phosgene type compound to the compound of formula III;

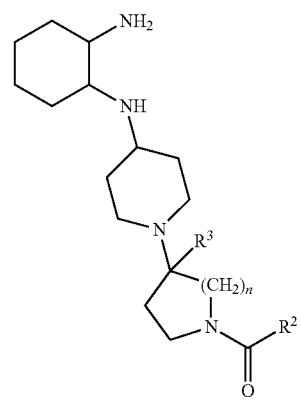

V wherein R², R³ and n are defined above.

Optionally, the step a) is carried out in the presence of a reducing agent, such as sodium borohydride, NaH(OAc)₃ or equivalence thereof.

Optionally, the phosgene type compound is selected from phosgene, triphosgene, 1,1'-carbonyldiimidazole and equivalence thereof.

In another embodiment, the invention provides an intermediate of formula V, a pharmaceutically acceptable salt thereof, diastereomer, enantiomer, or mixture thereof

V

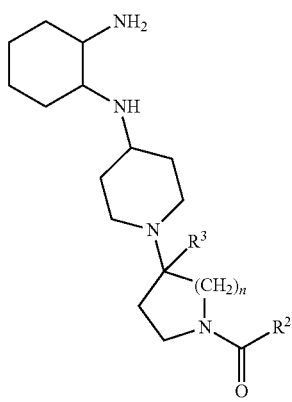

wherein $R^2$, $R^3$ and n are as defined above.

In a further embodiment, the invention provides an intermediate of formula IV, a pharmaceutically acceptable salt thereof, diastereomer, enantiomer, or mixture thereof:

IV

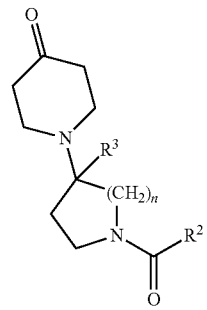

wherein $R^2$, $R^3$ and n are as defined above. In a particular embodiment, n of formula IV is 1. In another particular embodiment, n of formula IV is 1, 3 or 4.

Compounds of the present invention may also be prepared according to the synthetic routes as depicted in Schemes 1-4.

Scheme 1 (Examples 1-3, 16-18)

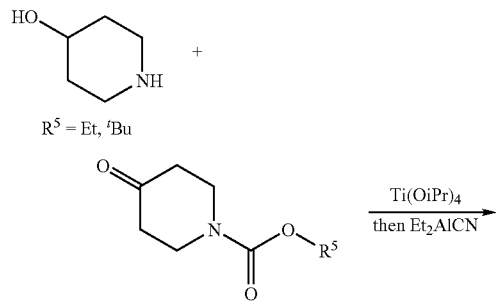

$R^5$ = Et, $^t$Bu

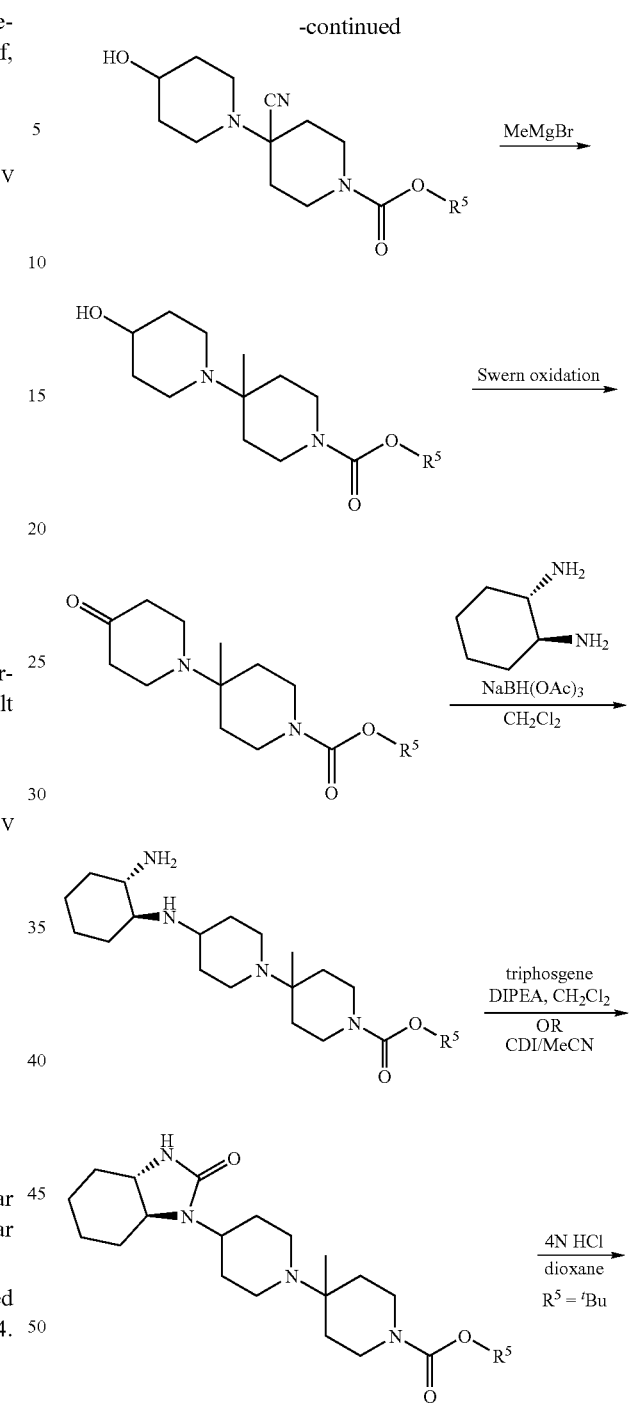

Example 1
$R^5$ = Ethyl

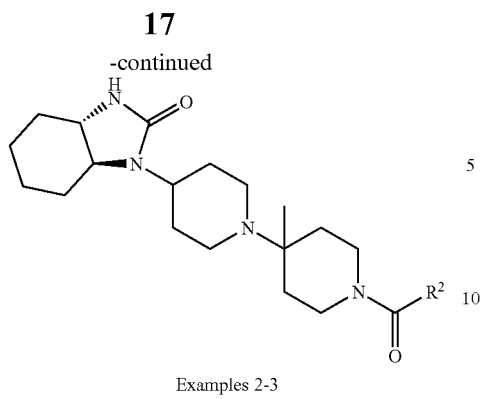
Examples 2-3
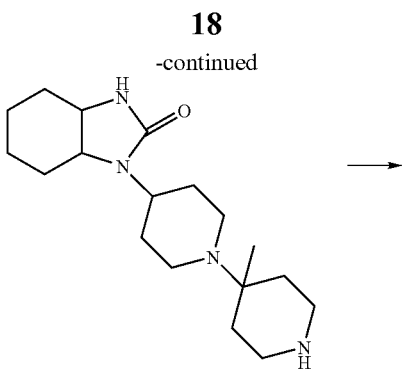
Examples 4-6, 12, 13
Scheme 2 (Examples 4-6, 12, 13)
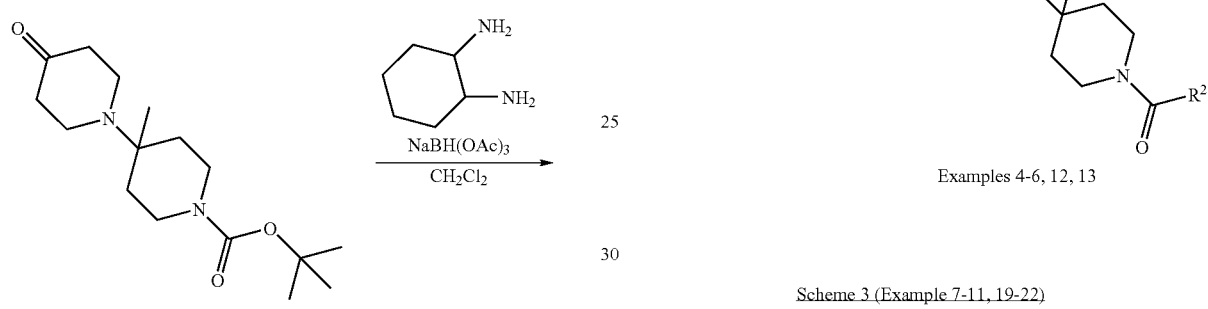
Scheme 3 (Example 7-11, 19-22)
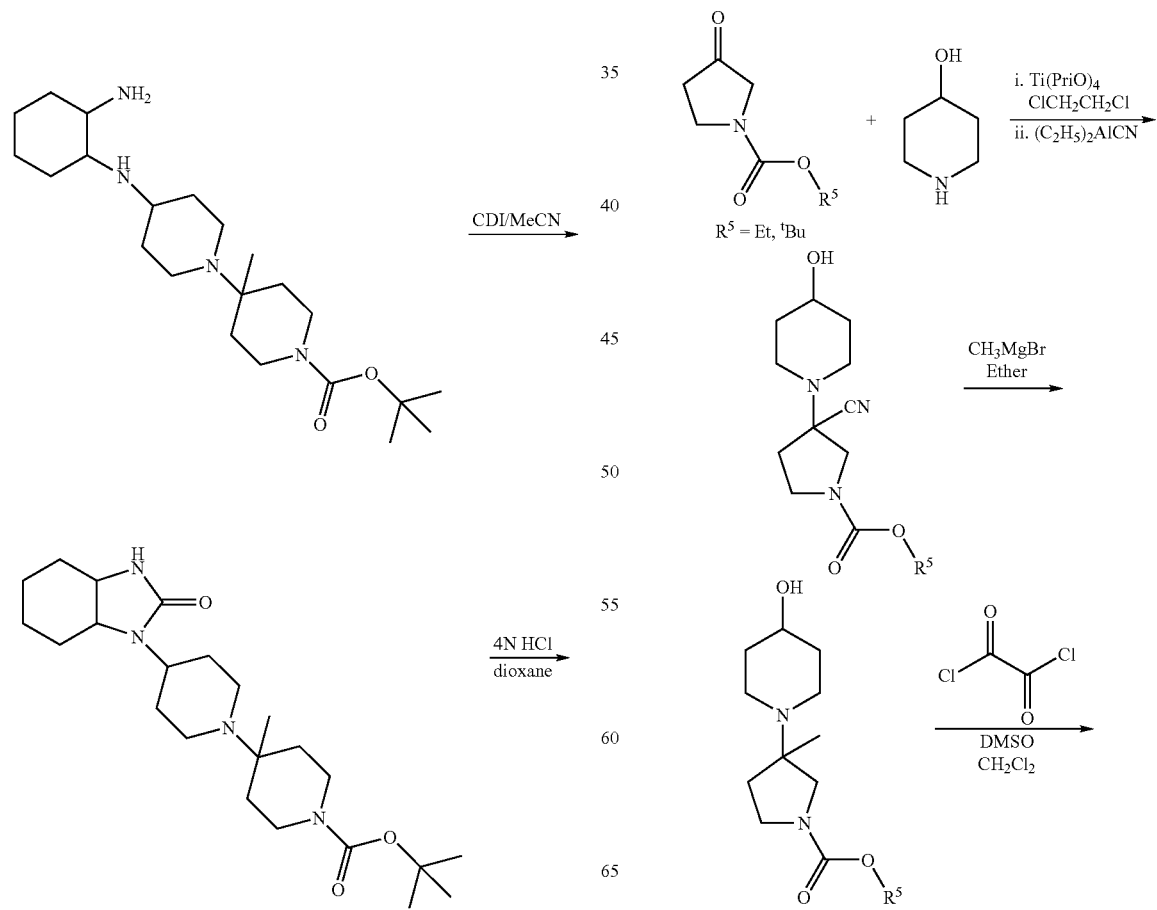

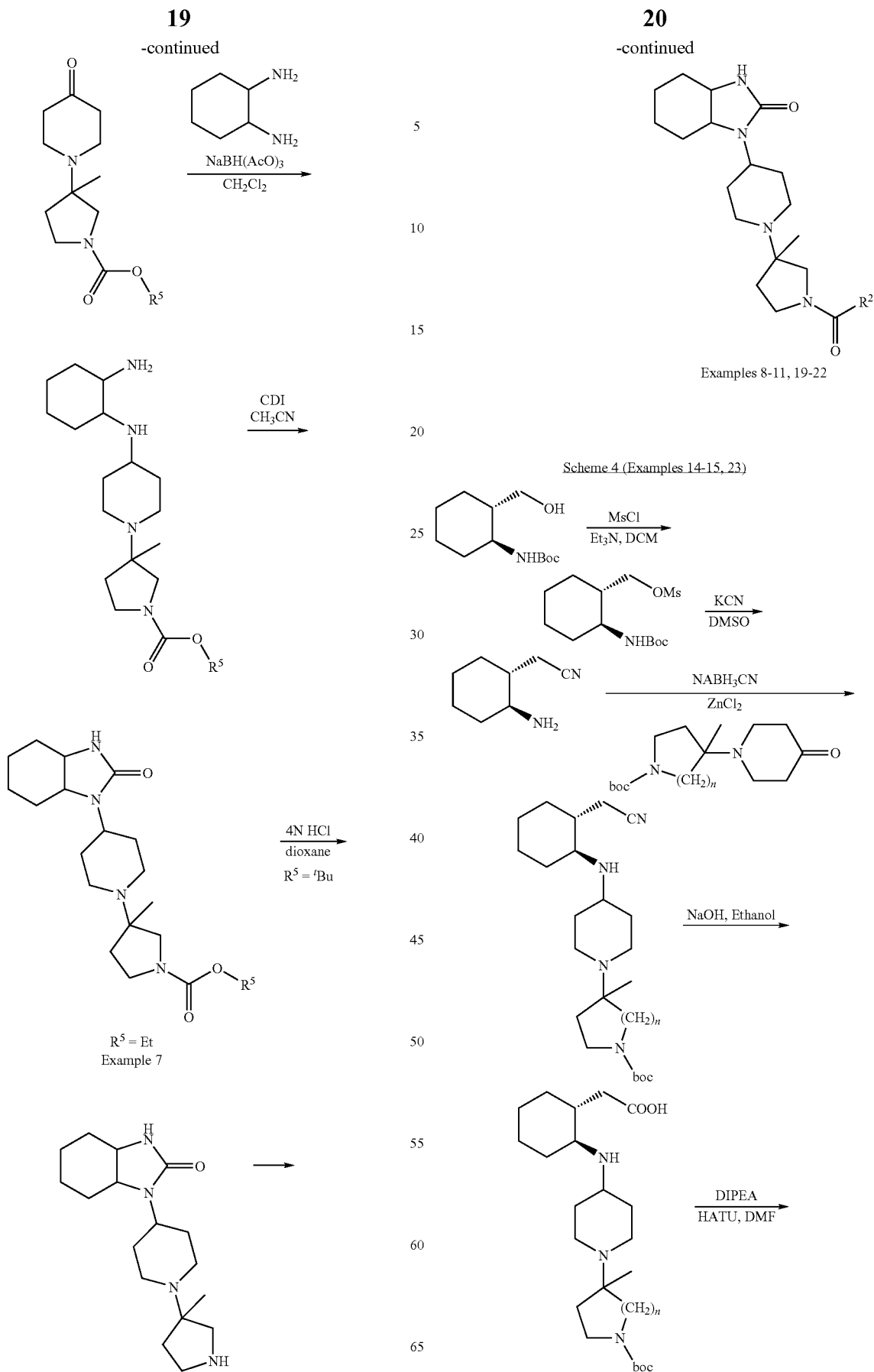

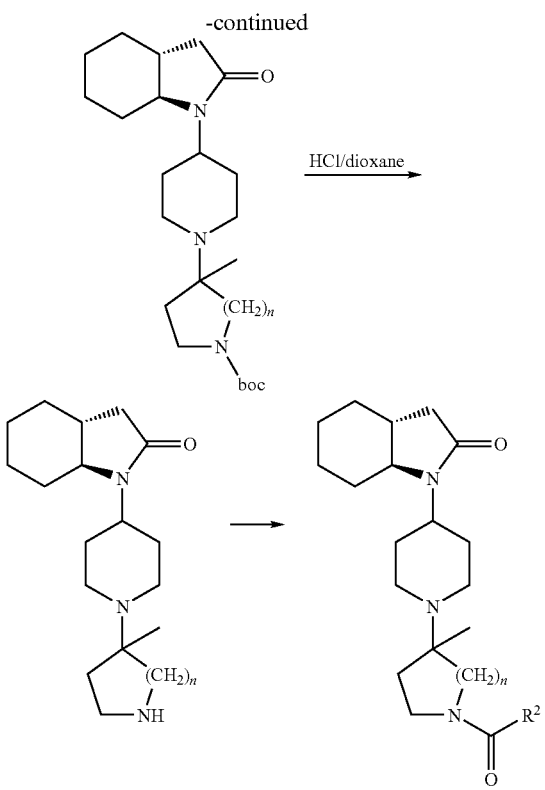

Biological Evaluation
Human M1, Rat M1, Human M3 and Human M5 Calcium Mobilization FLIPR™ Assay The compound activity in the present invention (EC50 or IC50) is measured using a 384 plate-based imaging assay that monitors drug induced intracellular $Ca^2$ release in whole cells. Activation of hM1 (human Muscarinic receptor subtype 1, gene bank access NM_000738), rM1 (rat Muscarinic receptor subtype 1, gene bank access NM_080773), hM3 (human Muscarinic receptor subtype 3, gene bank access NM_000740NM_000740) and hM5 (human Muscarinic receptor subtype 5, gene bank access NM_0121258), receptors expressed in CHO cells (Chinese hamster ovary cells, ATCC) is quantified in a Molecular Devices FLIPR II™ instrument as an increase in fluorescent signal. Inhibition of hM3 and hM5 by compounds is determined by the decrease in fluorescent signal in response to 2 nM acetylcholine activation.

CHO cells are plated in 384-well black/clear bottom poly-D-lysine plates (Becton Dickinson, 4663) at 8000 cells/well/50 µl for 24 hours in a humidified incubator (5% CO2 and 37° C.) in DMEM/F12 medium (Wisent 319-075-CL) without selection agent. Prior to experiment, the cell culture medium is removed from the plates by inversion. A loading solution of 25 µl of Hank's balanced salt solution 1× (Wisent 311-506-CL), 10 mM Hepes (Wisent 330-050-EL) and 2.5 mM Probenicid at pH 7.4 (Sigma Aldrich Canada P8761-100 g) with 2 µM calcium indicator dye (FLUO-4AM, Molecular Probes F14202) and Pluronic acid F-127 0.002% (Invitrogen P3000MP) is added to each well. Plates are incubated at 37° C. for 60 minutes prior to start the experiment. The incubation is terminated by washing the cells four times in assay buffer, leaving a residual 25 µl buffer per well. Cell plates are then transferred to the FLIPR, ready for compound additions.

The day of experiment, acetylcholine and compounds are diluted in assay buffer in three-fold concentration range (10 points serial dilution) for addition by FLIPR instrument. For all calcium assays, a baseline reading is taken for 10 seconds followed by the addition of 12.5 µl of compounds, resulting in a total well volume of 37.5 µl. Data is collected every second for 60 pictures and then every 6 seconds for 20 pictures prior to the addition of agonist. For hM3 and hM5, before agonist addition, a second baseline reading is taken for 10 seconds followed by the addition of 12.5 µl of agonist or buffer, producing a final volume of 50 µl. After agonist stimulation, the FLIPR continues to collect data every second for 60 pictures and then every 6 seconds for 20 pictures. The fluorescence emission is read using filter 1 (emission 510-570 nm) by the FLIPR on board CCD camera.

Calcium mobilization output data are calculated as the maximal relative fluorescence unit (RFU) minus the minimal value for both compound and agonist reading frame (except for hM1 and rM1 using only the maximal RFU). Data are analyzed using sigmoidal fits of a non-linear curve-fitting program (XLfit version 4.2.2 Excel add-in version 4.2.2 build 18 math 1Q version 2.1.2 build 18). All pEC50 and pIC50 values are reported as arithmetic means±standard error of mean of 'n' independent experiments.

hM2 Receptor GTPγS Binding

Membranes produced from Chinese hamster ovary cells (CHO) expressing the cloned human M2 receptor (human Muscarinic receptor subtype 2, gene bank access NM_000739), are obtained from Perkin-Elmer (RBHM2M). The membranes are thawed at 37° C., passed 3 times through a 23-gauge blunt-end needle, diluted in the GTPγS binding buffer (50 mM Hepes, 20 mM NaOH, 100 mM NaCl, 1 mM EDTA, 5 mM MgCl$_2$, pH 7.4, 100 µM DTT). The $EC_{50}$, $IC_{50}$ and $E_{max}$ of the compounds of the invention are evaluated from 10-point dose-response curves (three fold concentration range) done in 60 µl in 384-well non-specific binding surface plate (Corning). Ten microliters from the dose-response curves plate (5× concentration) are transferred to another 384 well plate containing 25 µl of the following: 5 µg of hM2 membranes, 500 µg of Flashblue beads (Perkin-Elmer) and GDP 25 µM. An additional 15 µl containing 3.3× (60,000 dpm) of GTPγ$^{35}$S (0.4 nM final) are added to the wells resulting in a total well volume of 50 µl. Basal and maximal stimulated [$^{35}$S]GTPγS binding are determined in absence and presence of 30 µM final of acetylcholine agonist. The membranes/beads mix are pre-incubated for 15 minutes at room temperature with 25 µM GDP prior to distribution in plates (12.5 µM final). The reversal of acetylcholine-induced stimulation (2 µM final) of [$^{35}$S]GTPγS binding is used to assay the antagonist properties ($IC_{50}$) of the compounds. The plates are incubated for 60 minutes at room temperature then centrifuged at 400 rpm for 5 minutes. The radioactivity (cpm) is counted in a Trilux (Perkin-Elmer).

Values of $EC_{50}$, $IC_{50}$ and $E_{max}$ are obtained using sigmoidal fits of a non-linear curve-fitting program (XLfit version 4.2.2 Excel add-in version 4.2.2 build 18 math 1Q version 2.1.2 build 18) of percent stimulated [$^{35}$S]GTPγS binding vs. log (molar ligand). All pEC50 and pIC50 values are reported as arithmetic means±standard error of mean of 'n' independent experiments.

hM4 Receptor GTPγS Binding

Membranes produced from Chinese hamster ovary cells (CHO) expressing the cloned human M4 receptor (human Muscarinic receptor subtype 4, gene bank access NM_000741), are obtained from Perkin-Elmer (RBHM4M). The membranes are thawed at 37° C., passed 3 times through a 23-gauge blunt-end needle, diluted in the GTPγS binding buffer (50 mM Hepes, 20 mM NaOH, 100 mM NaCl, 1 mM EDTA, 5 mM MgCl$_2$, pH 7.4, 100 µM DTT). The $EC_{50}$, $IC_{50}$ and $E_{max}$ of the compounds of the invention are evaluated from 10-point dose-response curves (three fold concentration range) done in 60 µl in 384-well non-specific binding surface plate (Corning). Ten microliters from the dose-response curves plate (5× concentration) are transferred to another 384 well plate containing 25 µl of the following: 10 µg of hM4 membranes, 500 µg of Flashblue beads (Perkin-Elmer) and GDP 40 µM. An additional 15 µl containing 3.3× (60,000 dpm) of GTPγ$^{35}$S (0.4 nM final) are added to the wells resulting in a total well volume of 50 µl. Basal and maximal stimulated [$^{35}$S]GTPγS binding are determined in absence and presence of 30 µM final of acetylcholine agonist. The membranes/beads mix are pre-incubated for 15 minutes at room temperature with 40 µM GDP prior to distribution in plates (20 µM final). The reversal of acetylcholine-induced stimulation (10 µM final) of [$^{35}$S]GTPγS binding is used to assay the antagonist properties ($IC_{50}$) of the compounds. The plates are incubated for 60 minutes at room temperature then centrifuged at 400 rpm for 5 minutes. The radioactivity (cpm) is counted in a Trilux (Perkin-Elmer).

Values of $EC_{50}$, $IC_{50}$ and $E_{max}$ are obtained using sigmoidal fits of a non-linear curve-fitting program (XLfit version 4.2.2 Excel add-in version 4.2.2 build 18 math 1Q version 2.1.2 build 18) of percent stimulated [$^{35}$S]GTPγS binding vs. log (molar ligand). All pEC50 and pIC50 values are reported as arithmetic means±standard error of mean of 'n' independent experiments.

Certain biological properties of certain compounds of the invention measured using one or more assays described above are listed in Table 1 below.

TABLE 1

Certain Biological Properties of the Certain Compounds of the Invention.

| Example No | hM1 EC50 (nM) | hM2 EC50 (nM) | hM3 EC50 (nM) | hM4 EC50 (nM) | hM5 EC50 (nM) |
|---|---|---|---|---|---|
| Example 01 | 1.9 | 45 | 1400 | >1200 | 49.9 |
| Example 02 | 4.4 | >200 | >40000 | >30000 | >40000 |
| Example 03 | <7.1 | >1600 | >40000 | >6500 | >40000 |
| Example 04 | 3.3 | 480 | >4200 | >6100 | 586 |
| Example 05 | 25 | >14000 | >49000 | >30000 | >49200 |
| Example 06 | 51 | >30000 | >49000 | >30000 | >49200 |
| Example 07 | 14 | 2300 | >40000 | >21000 | 1100 |
| Example 08 | 69 | >15000 | | >30000 | |
| Example 09 | <3.6 | >1000 | >40000 | >13000 | 313 |
| Example 10 | 69 | >4000 | | >30000 | |
| Example 11 | 55 | 2900 | | >30000 | |
| Example 12 | 11 | 130 | >40000 | >4000 | 919 |
| Example 13 | 54 | >30000 | >40000 | >30000 | >40000 |
| Example 14 | 19 | >30000 | >40000 | >30000 | >40000 |
| Example 15 | 36 | >15000 | >40000 | >30000 | >40000 |
| Example 16 | 3.6 | 121 | >40000 | >90000 | >40000 |
| Example 17 | 1.5 | 48 | | >30000 | |
| Example 18 | 66.6 | 2336 | >40000 | >30000 | >40000 |
| Example 19 | 4.9 | 204 | | 919 | |
| Example 20 | 257 | | | | |
| Example 21 | 18.4 | 4871 | >22110 | >90000 | >8413 |
| Example 22 | 3 | 1171 | >25610 | 3468 | 412 |
| Example 23 | 22 | 2675 | >120000 | 16950 | >120000 |

Rat SNL Heat Hyperalgesia Assay

Rats undergo spinal nerve ligation surgery as described in Kim and Chung (1992) (reference 1). Briefly, rats are anesthetized with isoflurane, the left L5 and L6 are isolated and tightly ligated with 4-0 silk thread. The wound is closed by suturing and applying tissue adhesive. Compound testing is performed at day 9 to day 36 post-surgery.

For behavioral testing, the animals are acclimatized to the test room environment for a minimum of 30 min. In order to assess the degree of hyperalgesia, the animals are placed on a glass surface (maintained at 30° C.), and a heat-source is focused onto the plantar surface of the left paw. The time from the initiation of the heat until the animal withdraws the paw is recorded. Each animal is tested twice (with an interval of 10 min between the two tests). A decrease in Paw Withdrawal Latency (PWL, average of the two tests) relative to naïve animals indicates a hyperalgesic state. The rats with a PWL of at least 2 seconds less than average PWL of Naïve group are selected for compound testing.

Each individual experiment consists of several groups of SNL rats, one group receiving vehicle while the other groups receive different doses of the test article. In all experiments, animals are tested for heat hyperalgesia using the plantar test before drug or vehicle administration to ensure stable heat-hyperalgesia baseline and rats are evenly divided into groups for compound testing. At a suitable interval after vehicle or drug administration, another test is performed to measure PWL. Generally, results from 2 individual experiments are pooled together and the data are presented as the mean paw withdrawal latency (PWL) (s)±standard error of mean (SEM).

Combination Therapy (Morphine and M1 Agonist According to Present Invention) in Rat SNL Heat Hyperalgesia Assay A combination containing a compound of the present invention and morphine at a predetermined ratio (e.g., 0.64:1) may be tested using this instant model. The combination drugs may be administered to the rats subcutaneously, orally or combination thereof, simultaneously or sequentially. The results (expressed as $ED_{50}$) for the combination may be compared with results obtained singly for the compound of the instant invention and morphine at the same or similar dosage range. If the $ED_{50}$ of the combination is significantly lower than the theoretical $ED_{50}$ calculated based on the $ED_{50}$ measured using the compound of the invention and morphine singly, then a synergy for the combination is indicated.

More specifically, a combination of morphine and the M1 agonist according to example 2 was investigated for treating neuropathic pain using the above disclosed Rat SNL heat hyperalgesia assay. Male Sprague Dawley rats (Harlan) weighing 200-250 g underwent spinal nerve ligation surgery as described in Kim and Chung (1992). Under isoflurane anesthesia, an incision was made dorsal to the lumbosacral plexus. The paraspinal muscles (left side) were separated from the spinous processes, the L5 and L6 spinal nerves isolated and tightly ligated with (4-0) silk suture distal to the dorsal root ganglion and prior to the entrance into the sciatic. The left L4 spinal nerve was left intact. The incision was closed and the skin was sealed. Rats were allowed to recover and then placed in cages with soft bedding. All experiments were conducted between postoperative days 7-25. Naïve rats were selected as controls. In all cases, the experimenter was blind to the treatment. Doses were pH-adjusted between 6.5 and 7.5 and administered at a volume of 4 ml/kg. Morphine was administered subcutaneously in saline 30 minutes before testing. The compound of example 2 was administered per os in saline 60 minutes before testing. The combination of morphine and the compound of example 2 was administered at the predetermined ratio example 2:morphine of 1:1.56.

In order to assess the degree of heat hyperalgesia, the rats were individually placed in Plexiglas boxes on the glass surface (maintained at 30° C.) of a paw thermal stimulator system (Model 390, series 8, IITC Life Science, Woodland Hills, USA) and allowed to acclimate for 30 min. A thermal stimulus, in the form of a radiant heat beam was focused onto the plantar surface of the affected paw. In each test session, rats were tested twice at approximately 5 min apart. Paw withdrawal latencies (PWLs) were calculated as the mean of the two values. The results obtained are summarized in Table 2, below:

TABLE 2

ED50 for morphine, the compound of example 2
and combination therapy of 1 part of compound
of example 2 and 1.56 parts of morphine

| Drug | $ED_{50}$ μmol/kg |
|---|---|
| Morphine | 3.8 |
| Compound of example 2 | 2.4 |
| Combination of 1 part of the compound of example 2 and 1.56 parts of morphine | 0.47 |

As $ED_{50}$ for the combination is significantly lower than corresponding values for the components alone, it is concluded that the combination of morphine and the compound of example 2 has a synergistic effect.

EXAMPLES

The invention will further be described in more detail by the following Examples which describe methods whereby compounds of the present invention may be prepared, purified, analyzed and biologically tested, and which are not to be construed as limiting the invention.

Example 1

Ethyl 4-[4-[(3aS,7aS)-2-oxo-3a,4,5,6,7,7a-hexahydro-3H-benzoimidazol-1-yl]-1-piperidyl]-4-methyl-piperidine-1-carboxylate

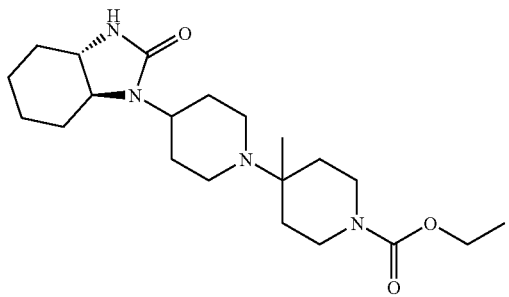

Step A. The preparation of ethyl 4-cyano-4-(4-hydroxy-1-piperidyl)piperidine-1-carboxylate

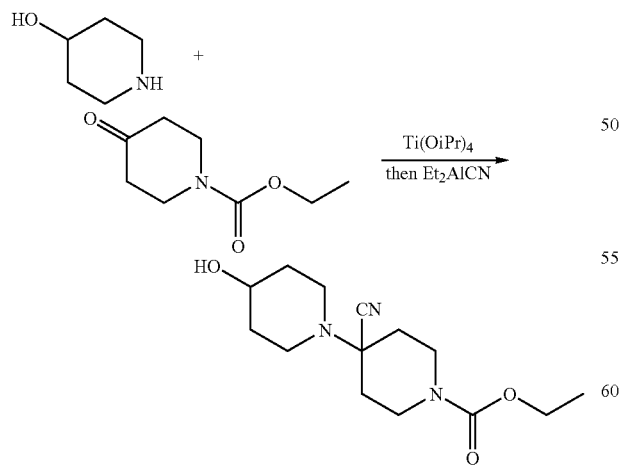

To a stirred solution of 4-hydroxypiperidine (1.01 g, 10.0 mmol) and ethyl 4-oxopiperidine-1-carboxylate (1.71 g, 10.0 mmol) in 1,2-dichloroethane (25 mL) was added titanium isopropoxide (2.3 mL, 11.0 mmol), and the mixture was stirred at room temperature for 18 h. Then a 1.0 M solution of diethylaluminum cyanide (24.0 mL, 24.0 mmol) was added at room temperature, stirred for 24 h, and diluted with EtOAc. The reaction was quenched at 0° C. with saturated NaHCO₃ (10 mL) and the mixture was further stirred for 2 h. The mixture was then filtered through Celite and the filtrate was concentrated in vacuo and purified by flash chromatography (ethyl acetate/hexane) to afford the title compound (2.45 g, 87%) as an oil. ¹H NMR (400 MHz, CHLOROFORM-D) δ ppm 1.19 (t, J=7.08 Hz, 3H), 1.45-1.67 (m, 4H), 1.85 (d, J=10.16 Hz, 2H), 2.00 (d, J=12.89 Hz, 2H), 2.20-2.28 (m, 2H), 2.81-2.92 (m, 2H), 3.04-3.23 (m, 3H), 3.58-3.71 (m, 1H), 3.81-3.98 (m, 2H), 4.06 (q, J=7.08 Hz, 2H).

Step B. The preparation of ethyl 4-(4-hydroxy-1-piperidyl)-4-methyl-piperidine-1-carboxylate

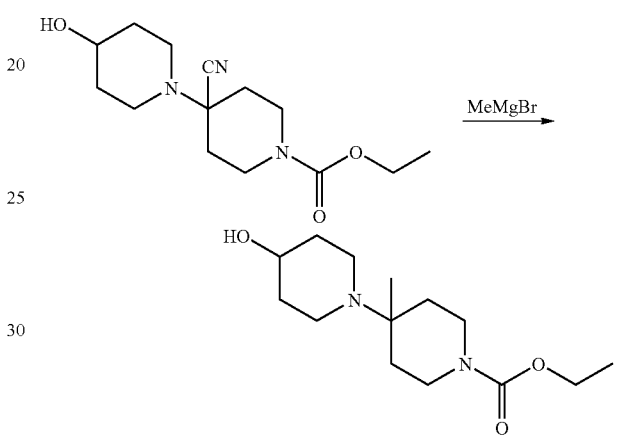

To a stirred solution of ethyl 4-cyano-4-(4-hydroxy-1-piperidyl)piperidine-1-carboxylate (2.45 g, 8.69 mmol) in THF (20 mL) was added a 1.4 M solution of MeMgBr in toluene/THF (18.6 mL, 26.1 mmol) at 0° C., and the mixture was stirred at room temperature for 12 h. The reaction was then quenched with saturated aqueous ammonium chloride, and the mixture was extracted with dichloromethane (2×25 mL). The combined extracts were concentrated in vacuo to afford the title compound (1.54 g, 65%), which was used in the next step without further purification. MS (M+1): 271.26.

Step C. The preparation of ethyl 4-methyl-4-(4-oxo-1-piperidyl)piperidine-1-carboxylate

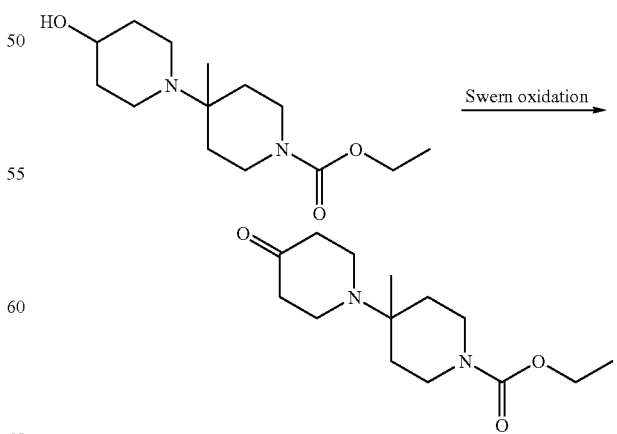

A solution of oxalyl chloride in dichloromethane (2M, 2.05 mL, 4.1 mmol) was cooled to −78° C. under nitrogen atmosphere and was added to a solution of dimethylsulfoxide (0.58 mL, 8.1 mmol) in dichloromethane (6 mL) at −78° C. under nitrogen atmosphere via cannula. After 10 minutes, a solution of ethyl 4-(4-hydroxy-1-piperidyl)-4-methyl-piperidine-1-carboxylate (2.7 mmol) in dichloromethane (3 mL) was added at −78° C. under nitrogen atmosphere to the reaction mixture via cannula. The mixture was stirred at −78° C. for 10 minutes and then triethylamine (1.51 mL, 10.8 mmol) was added dropwise. The reaction was stirred at −78° C. under nitrogen atmosphere for another 20 minutes, and then allowed to warm up to 0° C. over 1 hour. The reaction was quenched with water (10 mL) and diluted with dichloromethane (30 mL). The phases were separated and the aqueous layer was extracted with dichloromethane (2×25 mL). The combined organic phases were washed with saturated aqueous ammonium chloride, brine, dried over Na$_2$SO$_4$ and concentrated in vacuo to afford the title compound as yellow oil (672 mg, 93%), which was used for the subsequent step without further purification. $^1$H NMR (400 MHz, CHLOROFORM-D) δ ppm 0.96 (s, 3H), 1.24-1.30 (m, 3H), 1.39-1.53 (m, 2H), 1.72-1.92 (m, 2H), 2.11-2.30 (m, 1H), 2.42 (t, J=5.86 Hz, 2H), 2.51 (t, J=6.05 Hz, 1H), 2.81 (t, J=5.86 Hz, 2H), 2.97 (t, J=6.05 Hz, 1H), 3.22 (t, J=12.01 Hz, 1H), 3.35-3.47 (m, 2H), 3.53-3.72 (m, 2H), 4.14 (q, J=7.10 Hz, 2H). MS (M+1): 269.24.

Step D. The preparation of ethyl 4-[4-[[(1S,2S)-2-aminocyclohexyl]amino]-1-piperidyl]-4-methyl-piperidine-1-carboxylate

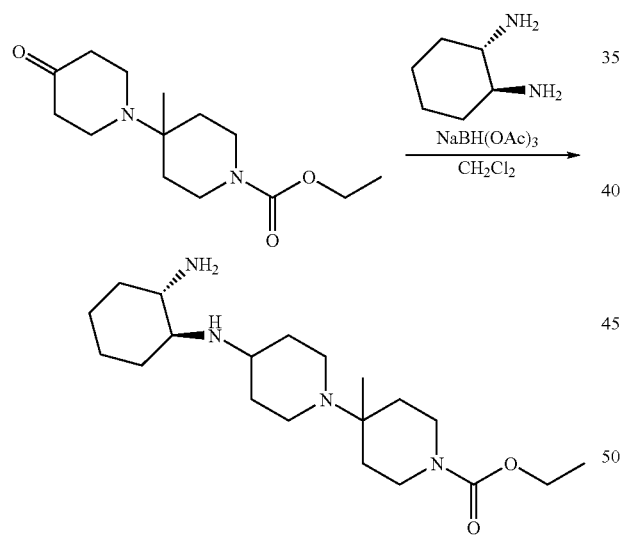

To a solution ethyl 4-methyl-4-(4-oxo-1-piperidyl)piperidine-1-carboxylate (336 mg, 1.25 mmol) and (1S,2S)-cyclohexane-1,2-diamine (286 mg, 0.5 mmol) in dichloromethane (10 mL) was added sodium triacetoxyborohydride (398 mg, 1.88 mmol) and stirred at room temperature for 12 h. Saturated NaHCO$_3$ (5 mL) was added, the phases were separated and the aqueous phase was extracted with dichloromethane (2×10 mL). The combined organic phases were washed with brine, dried over Na$_2$SO$_4$ and concentrated in vacuo. The residue was purified by passing through a short silica gel pad (5-10% MeOH in dichloromethane) to afford the title compound (87 mg, 19%). MS (M+1): 367.31.

Step E. The preparation of ethyl 4-[4-[(3aS,7aS)-2-oxo-3a,4,5,6,7,7a-hexahydro-3H-benzoimidazol-1-yl]-1-piperidyl]-4-methyl-piperidine-1-carboxylate

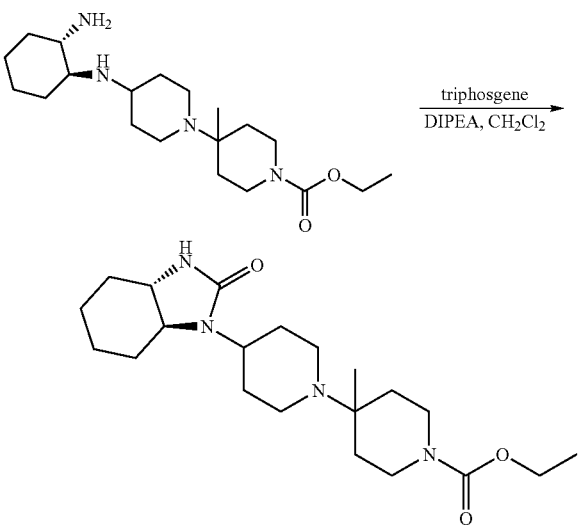

A solution of ethyl 4-[4-[[(1S,2S)-2-aminocyclohexyl]amino]-1-piperidyl]-4-methyl-piperidine-1-carboxylate (87 mg, 0.24 mmol) in dichloromethane (5 mL) was added with triphosgene (0.1 mmol) at 0° C. followed by with diisopropylethyl amine (0.5 mmol) and stirred at room temperature for 12 h. Water (2 mL) was added followed by dichloromethane (20 mL), the phases were separated and the aqueous phase was extracted with dichloromethane (2×10 mL). The combined organic phases were washed with brine, dried over Na$_2$SO$_4$ and concentrated in vacuo to give the crude product, which was purified with preparative LC/MS (high pH) to give the title compound as white solid 24 mg (25%). $^1$H NMR (400 MHz, METHANOL-D4) δ ppm 0.96 (s, 3H), 1.22 (t, J=7.08 Hz, 3H), 1.31-1.49 (m, 6H), 1.55-1.63 (m, 1H), 1.66-1.87 (m, 7H), 1.91-1.99 (m, 2H), 2.08-2.22 (m, 2H), 2.24-2.31 (m, 1H), 2.89-3.10 (m, 4H), 3.33-3.43 (m, 2H), 3.45-3.53 (m, 2H), 3.54-3.63 (m, 1H), 4.08 (q, J=7.08 Hz, 2H). MS (M+1): 393.3.

Example 2

Propan-2-yl 4-[4-[(3aS,7aS)-2-oxo-3a,4,5,6,7,7a-hexahydro-3H-benzoimidazol-1-yl]-1-piperidyl]-4-methyl-piperidine-1-carboxylate

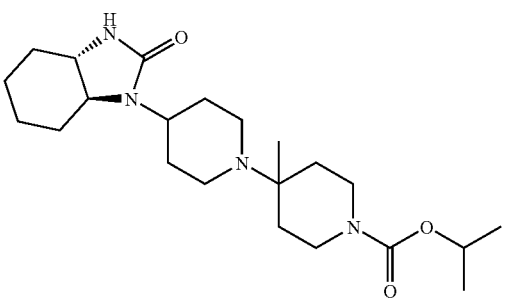

Step A. The preparation of tert-butyl 4-cyano-4-(4-hydroxy-1-piperidyl)piperidine-1-carboxylate

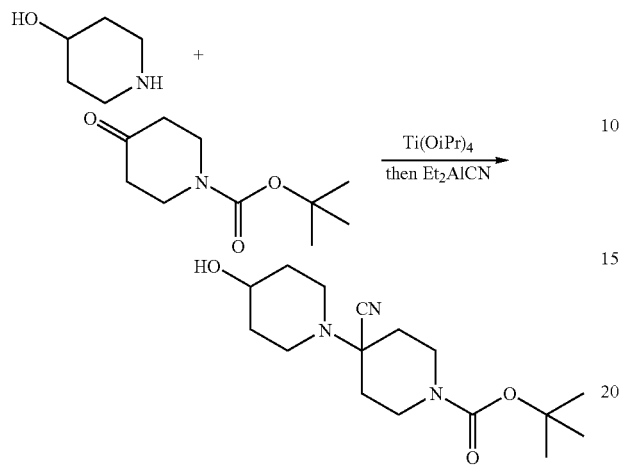

To a stirred solution of 4-hydroxypiperidine (2.02 g, 20.0 mmol) and tert-butyl 4-oxopiperidine-1-carboxylate (3.99 g, 20.0 mmol) in 1,2-dichloroethane (50 mL) was added titanium isopropoxide (4.6 mL, 22.0 mmol) and the mixture was stirred for 18 h at room temperature. A solution of diethylaluminum cyanide in toluene (1M, 48.0 mL, 48.0 mmol) was added and stirred at room temperature for 24 h. Diluted with EtOAc and the reaction was quenched at 0° C. with saturated NaHCO₃ (20 mL). The mixture was stirred a further 2 h, filtered through Celite, and the resulting filtrate was concentrated in vacuo to afford the title compound (5.89 g, 95%) as white solid, which was used for the next step without further purification.

Step B. The preparation of tert-butyl 4-(4-hydroxy-1-piperidyl)-4-methyl-piperidine-1-carboxylate

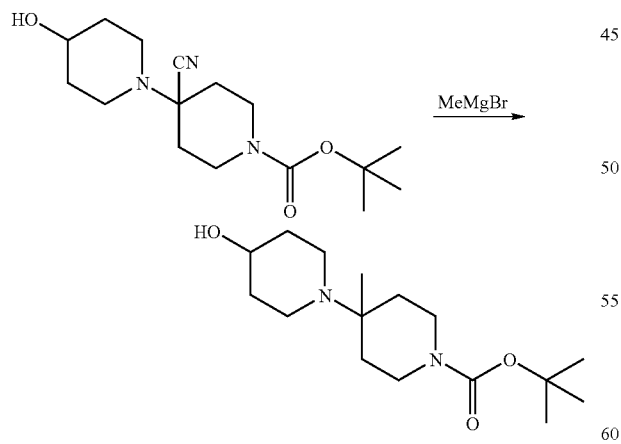

To a stirred solution of tert-butyl 4-cyano-4-(4-hydroxy-1-piperidyl)piperidine-1-carboxylate (5.8 g, 18.74 mmol) in THF (40 mL) was added a 1.4 M solution of MeMgBr in toluene/THF (26.8 mL, 37.48 mmol) at 0° C., and the mixture was stirred at room temperature for 12 h. The reaction was then quenched with saturated aqueous ammonium chloride and the mixture was extracted with dichloromethane (2×30 mL). The combined extracts were concentrated in vacuo to afford (5.42 g, 97%) the title compound, which was used for the next step without further purification.

MS (M+1): 299.24.

Step C. The preparation of tert-butyl 4-methyl-4-(4-oxo-1-piperidyl)piperidine-1-carboxylate

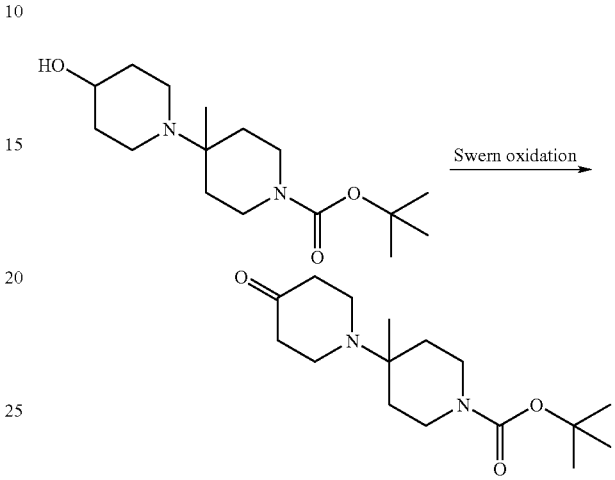

A solution of oxalyl chloride in dichloromethane (2M, 13.67 mL, 27.33 mmol) was cooled to −78° C. under nitrogen atmosphere and was added to a solution of dimethylsulfoxide (3.87 mL, 54.0 mmol) in dichloromethane (40 mL) at −78° C. under nitrogen atmosphere via cannula. After 10 minutes, a solution of tert-butyl 4-(4-hydroxy-1-piperidyl)-4-methyl-piperidine-1-carboxylate (18.0 mmol) in dichloromethane (20 mL) was added at −78° C. under nitrogen atmosphere to the reaction mixture via cannula. The mixture was stirred at −78° C. for 10 minutes and then triethylamine (10.07 mL, 72.0 mmol) was added dropwise. The reaction was stirred at −78° C. under nitrogen atmosphere for another 20 minutes, then allowed to warm up to 0° C. over 1 hour. The reaction was quenched with water (50 mL) and diluted with dichloromethane (100 mL). The phases were separated and the aqueous layer was extracted with dichloromethane (2×50 mL). The combined organic phases were washed with saturated aqueous ammonium chloride, brine, dried over Na₂SO₄ and concentrated in vacuo to afford the title compound as yellow oil (5.02 g, 94%), which was used for the subsequent step without further purification. MS (M+1): 297.24.

Step D. The preparation of tert-butyl 4-[4-[[(1S,2S)-2-aminocyclohexyl]amino]-1-piperidyl]-4-methyl-piperidine-1-carboxylate

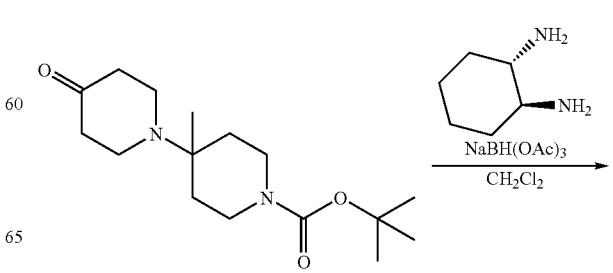

-continued

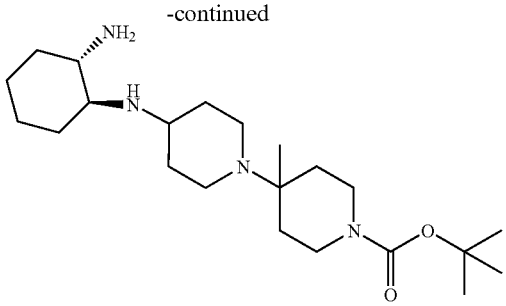

To a solution of tert-butyl 4-methyl-4-(4-oxo-1-piperidyl)piperidine-1-carboxylate (2.96 g, 10.0 mmol) and (1S,2S)-cyclohexane-1,2-diamine (2.29 g, 20.0 mmol) in dichloromethane (80 mL) was added sodium triacetoxyborohydride (3.18, 15.0 mmol) and stirred at room temperature for 12 h. Saturated NaHCO$_3$ (40 mL) was added, phases were separated and the aqueous layer was extracted with dichloromethane (2×60 mL). The combined organic phases were washed with brine, dried over Na$_2$SO$_4$ and concentrated in vacuo to afford the title compound, which was used for the subsequent step without further purification.

Step E. The preparation of tert-butyl 4-[4-[(3aS,7aS)-2-oxo-3a,4,5,6,7,7a-hexahydro-3H-benzoimidazol-1-yl]-1-piperidyl]-4-methyl-piperidine-1-carboxylate

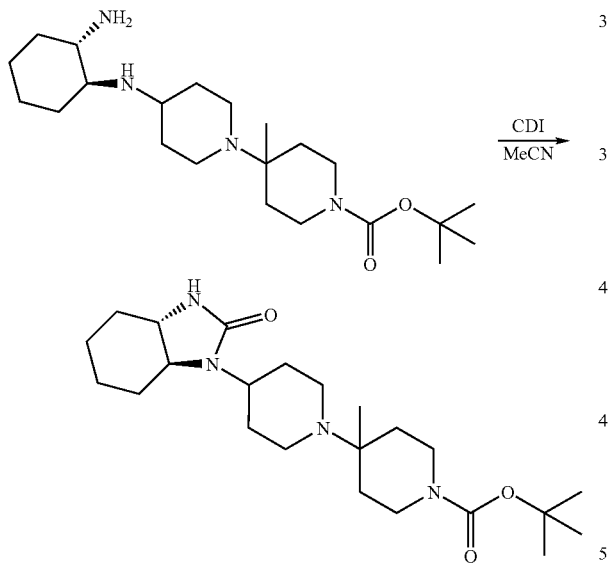

A solution of tert-butyl 4-[4-[[(1S,2S)-2-aminocyclohexyl]amino]-1-piperidyl]-4-methyl-piperidine-1-carboxylate (10.0 mmol) in acetonitrile (30 mL) was added with 1,1'-carbonyldiimidazole (1.95 g, 12.0 mmol) and stirred at room temperature for 12 h. Concentrated in vacuo and was added with water (20 mL) and dichloromethane (100 mL), phases were separated and the aqueous phase was extracted with dichloromethane (2×50 mL). The combined organic phases were washed with brine, dried over Na$_2$SO$_4$ and concentrated in vacuo. The residue was purified with preparative LC/MS (high pH) to provide the title compound as white solid (1.18 g, 28% over two steps). $^1$H NMR (400 MHz, METHANOL-D4) δ ppm 0.95 (s, 3H), 1.31-1.40 (m, 4H), 1.42 (s, 9H), 1.44-1.48 (m, 2H), 1.52-1.63 (m, 1H), 1.64-1.89 (m, 8H), 1.93-1.99 (m, 1H), 2.08-2.21 (m, 2H), 2.25-2.32 (m, 1H), 2.89-3.10 (m, 4H), 3.28-3.36 (m, 1H), 3.42-3.53 (m, 2H), 3.54-3.65 (m, 1H). MS (M+1): 421.3.

Step F. The preparation of (3aS,7aS)-1-[1-(4-methyl-4-piperidyl)-4-piperidyl]-3a,4,5,6,7,7a-hexahydro-3H-benzoimidazol-2-one

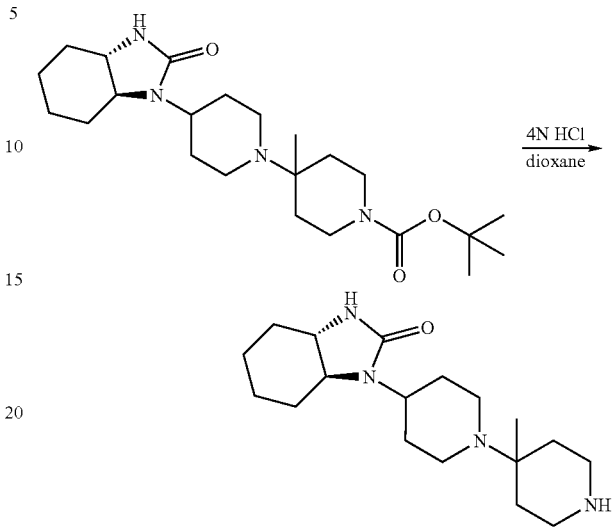

A solution of 4N HCl in dioxane (10 mL, 40.0 mmol) was added to tert-butyl 4-[4-[(3aS,7aS)-2-oxo-3a,4,5,6,7,7a-hexahydro-3H-benzoimidazol-1-yl]-1-piperidyl]-4-methyl-piperidine-1-carboxylate (1.18 g, 2.8 mmol) and the mixture was stirred at room temperature for 5 h. The solvent was removed in vacuo to afford the HCl salt of the title compound as white powder (1.05 g, 95%). MS (M+1): 321.25.

Step G. The preparation of propan-2-yl 4-[4-[(3aS,7aS)-2-oxo-3a,4,5,6,7,7a-hexahydro-3H-benzoimidazol-1-yl]-1-piperidyl]-4-methyl-piperidine-1-carboxylate

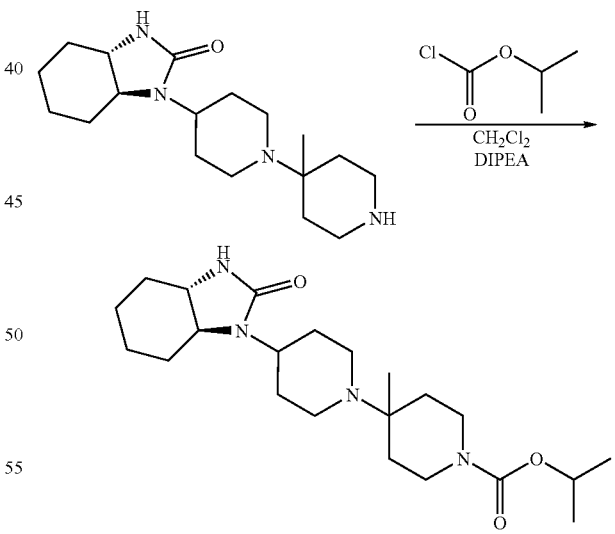

A solution of (3aS,7aS)-1-[1-(4-methyl-4-piperidyl)-4-piperidyl]-3a,4,5,6,7,7a-hexahydro-3H-benzoimidazol-2-one (HCl salt, 99 mg, 0.25 mmol) and diisopropylethylamine (129.3 mg, 1.0 mmol) in dry dichloromethane (5 mL) at 0° C. was added with a solution of 1.0 N isopropyl chloroformate in toluene (0.3 mL, 0.3 mmol) dropwise and stirred at room temperature for 3 h. Saturated NaHCO$_3$ (5 mL) was added followed by dichloromethane (20 mL). The phases were separated and the aqueous phase was extracted with dichloromethane (2×10 mL). The combined organic phases were washed with brine, dried over Na₂SO₄ and concentrated in vacuo. The residue was purified with preparative LC/MS (high pH) to give the title compound (49 mg, 48%). ¹H NMR (400 MHz, METHANOL-D4) δ ppm 0.95 (s, 3H), 1.21 (d, J=6.25 Hz, 6H), 1.31-1.49 (m, 6H), 1.52-1.64 (m, 1H), 1.65-1.88 (m, 7H), 1.95 (d, J=7.42 Hz, 1H), 2.10-2.20 (m, 2H), 2.26 (d, J=7.81 Hz, 1H), 2.89-3.15 (m, 4H), 3.31-3.44 (m, 2H), 3.42-3.51 (m, 2H), 3.53-3.64 (m, 1H), 4.78-4.90 (m, 1H). MS (M+1): 407.2.

Example 3

(3aS,7aS)-1-[1-[1-(cyclopropanecarbonyl)-4-methyl-4-piperidyl]-4-piperidyl]-3a,4,5,6,7,7a-hexahydro-3H-benzoimidazol-2-one

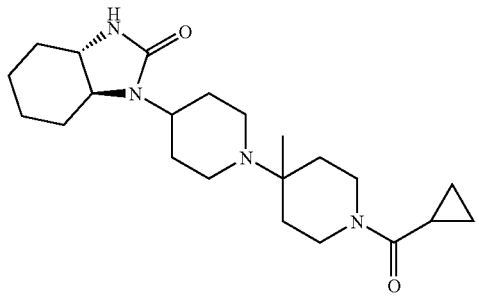

To the solution (3aS,7aS)-1-[1-(4-methyl-4-piperidyl)-4-piperidyl]-3a,4,5,6,7,7a-hexahydro-3H-benzoimidazol-2-one (99 mg, 0.25 mmol) in dry DMF (3 mL) was added cyclopropanecarboxylic acid (26 mg, 0.3 mmol) followed by HATU (114 mg, 0.3 mmol) and diisopropylethylamine (0.10 mL, 0.5 mmol) and stirred at room temperature for 1 h. The solvent was removed in vacuo, dichloromethane added (15 mL), washed with saturated NaHCO₃ (10 mL) and brine (10 mL), dried over Na₂SO₄ and concentrated in vacuo. The residue was purified with preparative LC/MS (high pH) to yield the title compound (59 mg, 61%) as white powder. ¹H NMR (400 MHz, METHANOL-D4) δ ppm 0.71-0.89 (m, 4H), 1.00 (s, 3H), 1.28-1.46 (m, 5H), 1.50-1.68 (m, 2H), 1.68-1.89 (m, 8H), 1.89-2.00 (m, 2H), 2.11-2.31 (m, 2H), 2.86-3.02 (m, 2H), 3.02-3.14 (m, 2H), 3.47-3.70 (m, 4H), 3.75-3.91 (m, 1H). MS (M+1): 389.2.

Example 4

Ethyl 4-[4-[(3aR,7aR)-2-oxo-3a,4,5,6,7,7a-hexahydro-3H-benzoimidazol-1-yl]-1-piperidyl]-4-methyl-piperidine-1-carboxylate

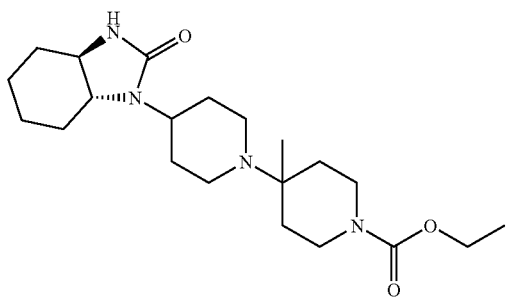

Step A. The preparation of tert-butyl 4-[4-[[(1R,2R)-2-aminocyclohexyl]amino]-1-piperidyl]-4-methyl-piperidine-1-carboxylate

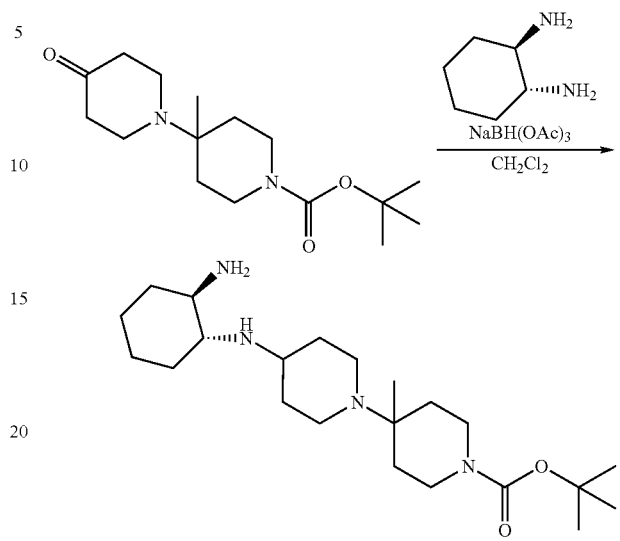

To a solution of tert-butyl 4-methyl-4-(4-oxo-1-piperidyl)piperidine-1-carboxylate (2.0 g, 6.76 mmol) and (1R,2R)-cyclohexane-1,2-diamine (1.55 g, 13.5 mmol) in dichloromethane (60 mL) was added sodium triacetoxyborohydride (2.12 g, 10.0 mmol) and stirred at room temperature for 12 h. Saturated NaHCO₃ (40 mL) was added, the phases were separated and the aqueous phase was extracted with dichloromethane (2×60 mL). The combined organic phases were washed with brine, dried over Na₂SO₄, and concentrated in vacuo. The crude product was used for the next step without further purification.

Step B. The preparation of tert-butyl 4-[4-[(3aS,7aS)-2-oxo-3a,4,5,6,7,7a-hexahydro-3H-benzoimidazol-1-yl]-1-piperidyl]-4-methyl-piperidine-1-carboxylate

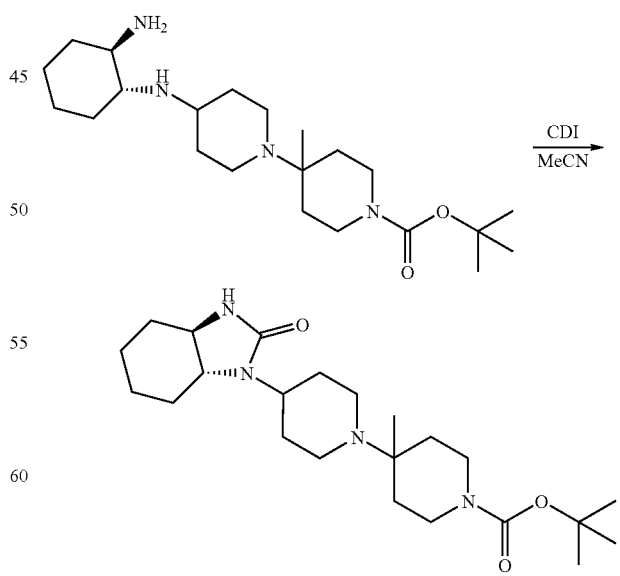

A solution of tert-butyl 4-[4-[[(1R,2R)-2-aminocyclohexyl]amino]-1-piperidyl]-4-methyl-piperidine-1-carboxylate in acetonitrile (20 mL) was added with 1,1'-carbonyldiimidazole (1.30 g, 8.0 mmol) and the reaction mixture was stirred at room temperature for 12 h. The solvent was removed in vacuo and the residue was taken up in water (20 mL) and dichloromethane (80 mL). The phases were separated and the aqueous phase was extracted with dichloromethane (2×50 mL). The combined organic phases were washed with brine, dried over $Na_2SO_4$, filtered, and concentrated in vacuo to give the crude product, which was purified with preparative LC/MS (high pH) to give the title compound as white solid (849 mg, 30% over two steps). 1H NMR (400 MHz, METHANOL-D4) δ ppm 0.95 (s, 3H), 1.31-1.40 (m, 4H), 1.42 (s, 9H), 1.44-1.48 (m, 2H), 1.52-1.63 (m, 1H), 1.64-1.89 (m, 8H), 1.93-1.99 (m, 1H), 2.08-2.21 (m, 2H), 2.25-2.32 (m, 1H), 2.89-3.10 (m, 4H), 3.28-3.36 (m, 1H), 3.42-3.53 (m, 2H), 3.54-3.65 (m, 1H). MS (M+1): 421.3.

Step C. The preparation of (3aR,7aR)-1-[1-(4-methyl-4-piperidyl)-4-piperidyl]-3a,4,5,6,7,7a-hexahydro-3H-benzoimidazol-2-one

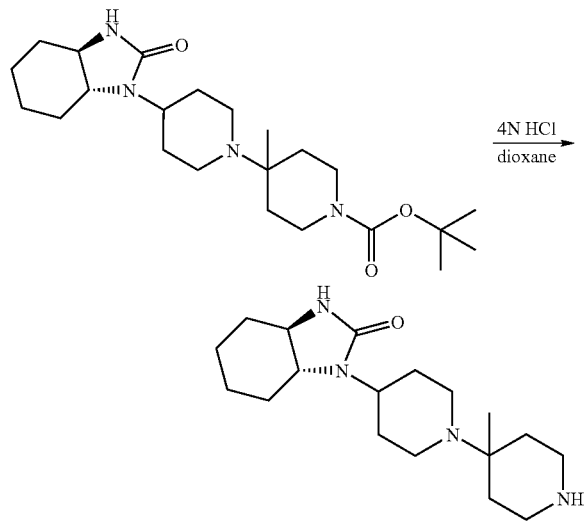

A solution of 4N HCl in dioxane (8 mL, 32.0 mmol) was added to tert-butyl 4-[4-[(3aS,7aS)-2-oxo-3a,4,5,6,7,7a-hexahydro-3H-benzoimidazol-1-yl]-1-piperidyl]-4-methyl-piperidine-1-carboxylate (849 mg, 2.02 mmol) and the mixture was stirred at room temperature for 5 h. Solvent was removed in vacuo to afford the HCl salt of the title compound (789 mg, 99%) as white solid. MS (M+1): 321.25.

Step D. The preparation of ethyl 4-[4-[(3aR,7aR)-2-oxo-3a,4,5,6,7,7a-hexahydro-3H-benzoimidazol-1-yl]-1-piperidyl]-4-methyl-piperidine-1-carboxylate

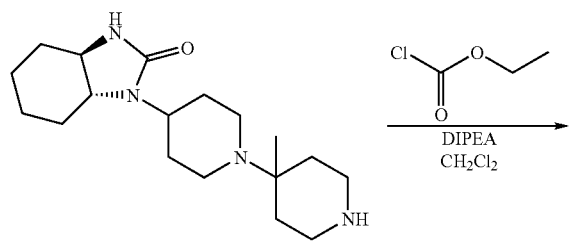

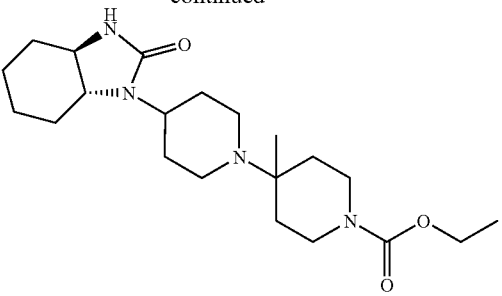

A solution of (3aR,7aR)-1-[1-(4-methyl-4-piperidyl)-4-piperidyl]-3a,4,5,6,7,7a-hexahydro-3H-benzoimidazol-2-one (HCl salt, 99 mg, 0.25 mmol) and diisopropylethylamine (129.3 mg, 1.0 mmol) in dry dichloromethane (5 mL) at 0° C. was added with a solution of 1.0 N ethyl chloroformate in dichloromethane (0.3 mL, 0.3 mmol) dropwise and was stirred at room temperature for 3 h. Saturated $NaHCO_3$ (5 mL) was added followed by dichloromethane (20 mL). The phases were separated and the aqueous phase was extracted with dichloromethane (2×10 mL). The combined organic phases were washed with brine, dried over $Na_2SO_4$ and concentrated in vacuo. The residue was purified with preparative LC/MS (high pH) to give the title compound (48 mg, 49%). $^1$H NMR (400 MHz, METHANOL-D4) δ ppm 0.99 (s, 3H), 1.21 (t, J=7.03 Hz, 3H), 1.31-1.54 (m, 6H), 1.58-2.00 (m, 9H), 2.06-2.35 (m, 3H), 2.88-3.04 (m, 2H), 3.04-3.18 (m, 2H), 3.29-3.44 (m, 2H), 3.48-3.69 (m, 3H), 4.08 (q, J=7.03 Hz, 2H). MS (M+1): 393.2.

Example 5

Propan-2-yl 4-[4-[(3aR,7aR)-2-oxo-3a,4,5,6,7,7a-hexahydro-3H-benzoimidazol-1-yl]-1-piperidyl]-4-methyl-piperidine-1-carboxylate

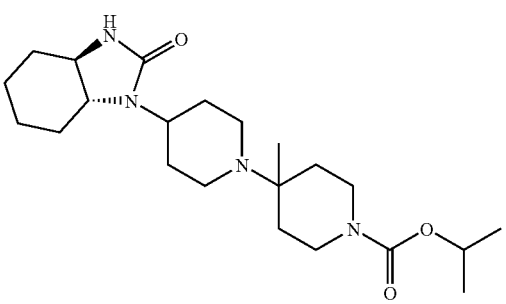

A solution of (3aR,7aR)-1-[1-(4-methyl-4-piperidyl)-4-piperidyl]-3a,4,5,6,7,7a-hexahydro-3H-benzoimidazol-2-one (HCl salt, 99 mg, 0.25 mmol) and diisopropylethylamine (129.3 mg, 1.0 mmol) in dry dichloromethane (5 mL) at 0° C. was added dropwise with a solution of 1.0 N isopropyl chloroformate in dichloromethane (0.3 mL, 0.3 mmol) and was stirred at room temperature for 3 h. Saturated $NaHCO_3$ (5 mL) was added followed by dichloromethane (20 mL). The phases were separated and the aqueous phase was extracted with dichloromethane (2×10 mL). The combined organic phases were washed with brine, dried over $Na_2SO_4$ and concentrated in vacuo. The residue was purified with preparative LC/MS (high pH) to give the title compound (52 mg, 51%). $^1$H NMR (400 MHz, METHANOL-D4) δ ppm 0.98 (s, 3H), 1.21 (d, J=6.25 Hz, 6H), 1.30-1.51 (m, 6H), 1.61 (d, J=11.33 Hz, 1H), 1.67-1.89 (m, 7H), 1.95 (d, J=7.42 Hz, 1H), 2.13-2.34 (m, 3H), 2.85-3.16 (m, 4H), 3.28-3.41 (m, 2H), 3.47-3.68 (m, 3H), 4.77-4.85 (m, 1H). MS (M+1): 407.3.

Example 6

(3aR,7aR)-1-[1-[1-(cyclopropanecarbonyl)-4-methyl-4-piperidyl]-4-piperidyl]-3a,4,5,6,7,7a-hexahydro-3H-benzoimidazol-2-one

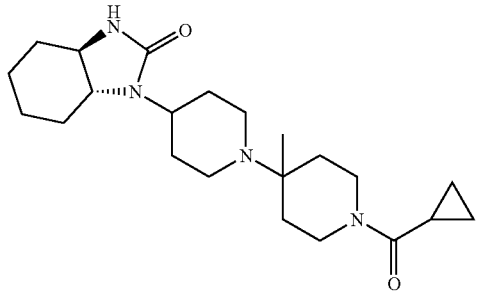

To the solution (3aR,7aR)-1-[1-(4-methyl-4-piperidyl)-4-piperidyl]-3a,4,5,6,7,7a-hexahydro-3H-benzoimidazol-2-one (HCl salt, 99 mg, 0.25 mmol) in dry DMF (3 mL) was added cyclopropanecarboxylic acid (26 mg, 0.3 mmol) followed by HATU (114 mg, 0.3 mmol) and diisopropylethylamine (0.10 mL, 0.5 mmol) and the mixture was stirred at room temperature for 1 h. The solvent was removed in vacuo, the residue dissolved in dichloromethane (15 mL), washed with saturated NaHCO$_3$ (10 mL) and brine (10 mL), dried over Na$_2$SO$_4$ and concentrated in vacuo. The residue was purified with preparative LC/MS (high pH) to afford the title compound (27 mg, 28%) as white powder. $^1$H NMR (400 MHz, METHANOL-D4) δ ppm 0.63-0.81 (m, 4H), 0.97 (s, 3H), 1.23-1.43 (m, 5H), 1.51-1.82 (m, 9H), 1.83-1.95 (m, 3H), 2.06-2.29 (m, 2H), 2.81-3.00 (m, 2H), 2.98-3.14 (m, 2H), 3.33-3.64 (m, 4H), 3.70-3.88 (m, 1H). MS (M+1): 389.2.

Example 7

Ethyl 3-[4-[(3aS,7aS)-2-oxo-3a,4,5,6,7,7a-hexahydro-3H-benzoimidazol-1-yl]-1-piperidyl]-3-methyl-pyrrolidine-1-carboxylate (mixture of diastereomers)

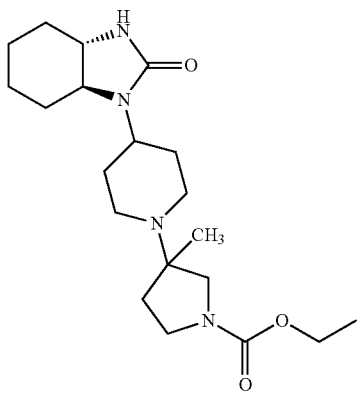

Step A. The preparation of ethyl 3-cyano-3-(4-hydroxy-1-piperidyl)pyrrolidine-1-carboxylate

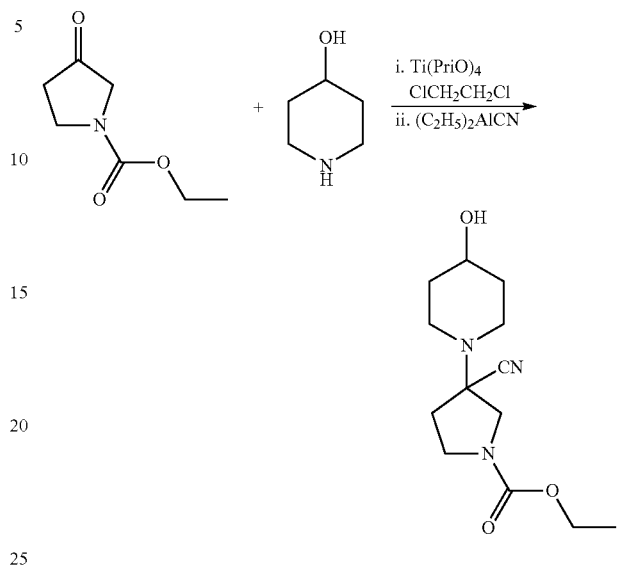

To a stirred solution of 4-hydroxypiperidine (464 mg, 4.58 mmol) and ethyl 3-oxopyrrolidine-1-carboxylate (610 mg, 3.82 mmol) in 1,2-dichloroethane (25 mL) was added titanium isopropoxide (1.09 g, 3.82 mmol), and the mixture was stirred at room temperature overnight. Then a 1.0 M solution of diethylaluminum cyanide (1.02 g, 9.17 mmol) was added at room temperature and the mixture was stirred for 24 h. Diluted with dichloromethane (25 mL) and quenched with saturated ammonium chloride solution (10 mL) at 0° C. Then mixture was filtered through a small pad of celite, and the resulting filtrate was concentrated in vacuo to afford the title compound as a yellow gum (1.0 g). $^1$H NMR (CDCl$_3$, 400 MHz): δ 4.22 (q, 2H), 4.21-4.1 (dd, 1H), 3.79-3.62 (m, 3H), 3.38 (dd, 1H), 2.9 (brs, 1H), 2.7 (brs, 1H), 2.54-2.35 (m, 3H), 2.18-1.85 (brm, 3H), 1.68-1.45 (m, 3H), 1.25 (t, 3H). MS (M+1): 268.14.

Step B. The preparation of ethyl 3-(4-hydroxy-1-piperidyl)-3-methyl-pyrrolidine-1-carboxylate

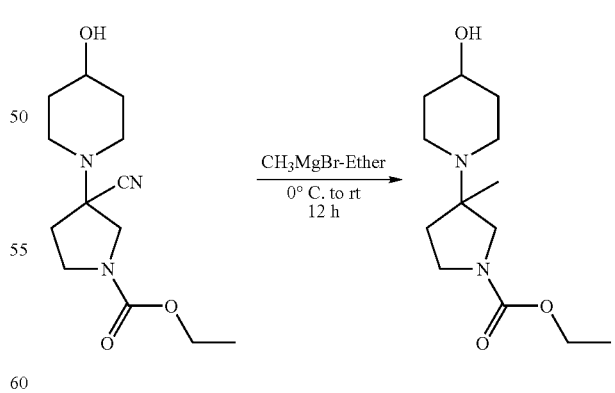

To a stirred solution of ethyl 3-cyano-3-(4-hydroxy-1-piperidyl)pyrrolidine-1-carboxylate (1.0 gm, 3.74 mmol) in tetrahydrofuran (25 mL) was added a 1.4 M solution of methyl magnesium bromide in toluene/THF (5.35 mL, 7.48 mmol) at 0° C., and the mixture was allowed to warm to room temperature. The mixture was stirred for another 12 h at room temperature, the reaction was quenched with saturated ammonium chloride solution (5 mL) at 0° C. and diluted with ethyl acetate (25 mL). The layers were separated and the organic layer was washed with brine, dried over anhydrous Na$_2$SO$_4$ and concentrated in vacuo to afford the title compound as a pale solid (830 mg), which was used for the subsequent step without further purification. MS (M+1): 257.16.

Step C. The preparation of ethyl 3-methyl-3-(4-oxo-1-piperidyl)pyrrolidine-1-carboxylate

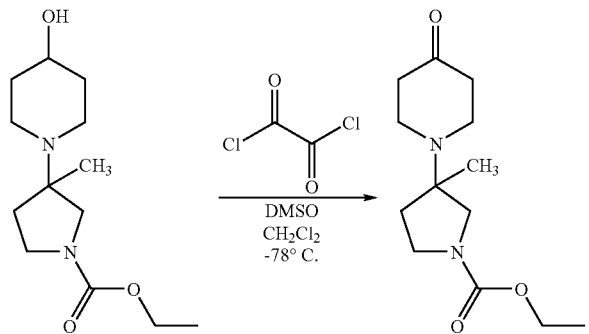

2M Oxalyl chloride solution in dichloromethane (617 mg, 4.86 mmol) was taken into a oven dried round bottom flak and cooled to −78° C. under nitrogen atmosphere. Then dimethyl sulfoxide (767 mg, 9.72 mmol) in anhydrous dichloromethane (5 mL) was added dropwise. After 10 minutes, a solution of ethyl 3-(4-hydroxy-1-piperidyl)-3-methyl-pyrrolidine-1-carboxylate (830 mg, 3.24 mmol) in dichloromethane (10 mL) was cannulated into the flask and stirred at −78° C. for another 10 minutes. Triethylamine (1.31 g, 12.96 mmol) was then added and stirred at −78° C. for 30 minutes, allowed to warm to 0° C. over 30 minutes and was quenched with saturated solution of ammonium chloride (10 mL). The product was extracted into dichloromethane (2×50 mL) and the combined organic layers were washed with brine, dried over anhydrous Na$_2$SO$_4$ and concentrated in vacuo to afford the title compound as a yellow oil (810 mg, 90%). $^1$H NMR (CDCl$_3$, 400 MHz): δ 4.18 (m, 2H), 3.88 (m, 1H), 3.62-3.35 (m, 3H), 2.92 (m, 1H), 2.85 (brs, 2H), 2.75 (brs, 1H), 2.48-2.39 (m, 4H), 2.05-1.89 (m, 1H), 1.41 (m, 1H), 1.26 (t, 3H), 1.08 (s, 3H) MS (M+1): 255.12.

Step D. The preparation of ethyl 3-[4-[[(1S,2S)-2-aminocyclohexyl]amino]-1-piperidyl]-3-methyl-pyrrolidine-1-carboxylate (mixture of diastereomers)

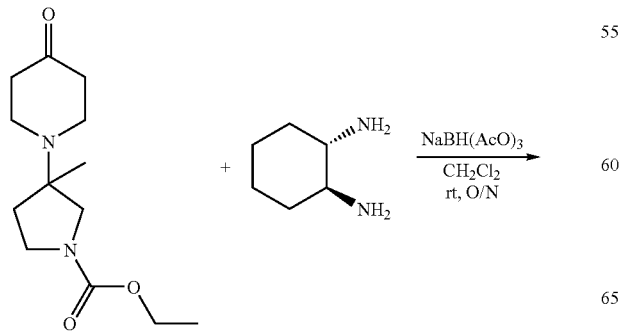

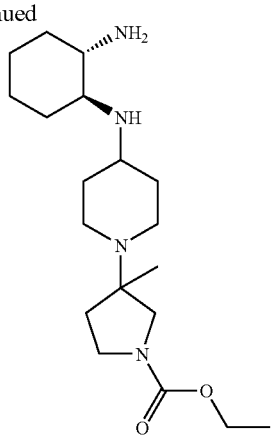

A solution of ethyl 3-methyl-3-(4-oxo-1-piperidyl)pyrrolidine-1-carboxylate (810 mg, 3.19 mmol) and 1S,2S-diaminocyclohexane (733.2 mg, 6.638 mmol) in anhydrous dichloromethane (20 mL) was added with sodium triacetoxyborohydride (946.5 mg, 4.47 mmol) and stirred at room temperature over night. Then reaction was quenched with 5% sodium bicarbonate solution, stirred for 30 minutes and the product was extracted into dichloromethane (2×50 mL). The combined extracts were washed with brine, dried over anhydrous MgSO$_4$ and concentrated in vacuo to afford the title compound as white foam (600 mg), which was used for the subsequent step without further purification. MS (M+1): 353.39.

Step E. The preparation of ethyl 3-methyl-3-{4-[(3aS,7aS)-2-oxooctahydro-1H-benzimidazol-1-yl]piperidin-1-yl}pyrrolidine-1-carboxylate (mixture of diastereomers)

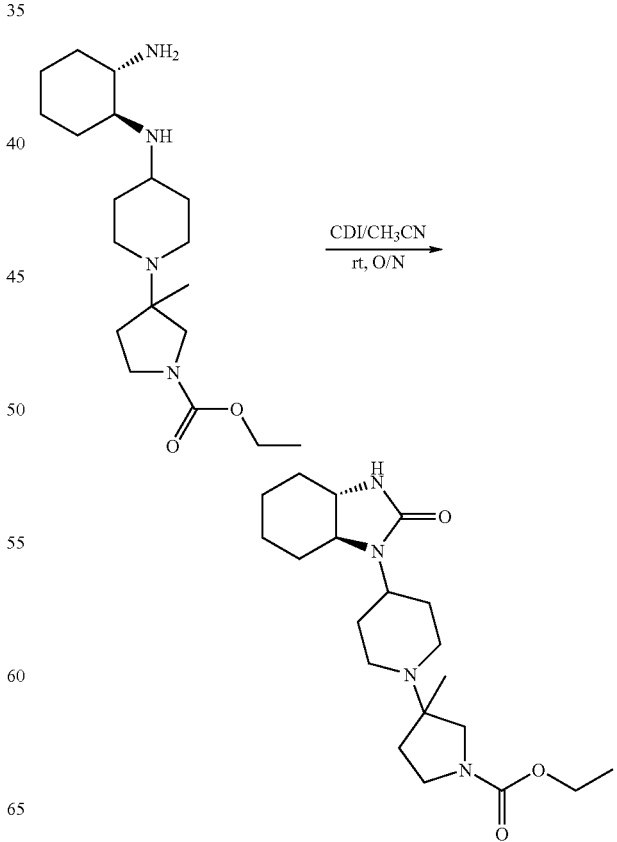

A solution of ethyl 3-[4-[[(1S,2S)-2-aminocyclohexyl]amino]-1-piperidyl]-3-methyl-pyrrolidine-1-carboxylate (600 mg, 1.70 mmol) in anhydrous acetonitrile (30 mL) was added with 1,1'-carbonyldiimidazole (551.92 mg, 3.40 mmol) and stirred at room temperature for 12 h. The solvent was removed in vacuo; the residue was dissolved in dichloromethane (60 mL), washed with water and brine and dried over anhydrous $MgSO_4$. Concentrated in vacuo and the residue was purified by flash chromatography (dichloromethane/methanol) to afford the title compound as a white solid (45 mg). $^1$H NMR ($CD_3OD$, 400 MHz): δ 4.15 (q, 2H), 3.62-3.51 (m, 2H), 2.41 (m, 2H), 3.22 (m, 1H), 3.19 (brd, 1H), 2.99 (m, 3H), 2.76 (brs, 1H), 2.45 (m, 3H), 2.01-1.82 (m, 6H), 1.74 (brd, 1H), 1.65 (brd, 1H), 1.45 (m, 4H), 1.25 (t, 3H), 1.12 (s, 3H). MS (M+1): 379.18.

Example 8

2-fluoroethyl 3-[4-[(3aS,7aS)-2-oxo-3a,4,5,6,7,7a-hexahydro-3H-benzoimidazol-1-yl]-1-piperidyl]-3-methyl-pyrrolidine-1-carboxylate (mixture of diastereomers)

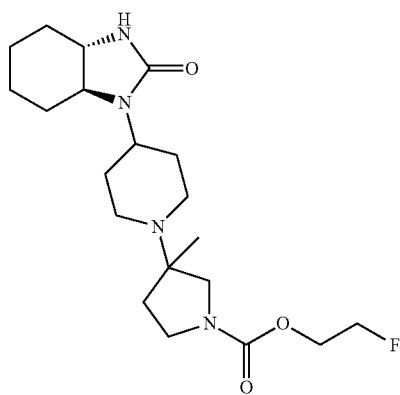

Step A. The preparation of tert-butyl 3-cyano-3-(4-hydroxy-1-piperidyl)pyrrolidine-1-carboxylate

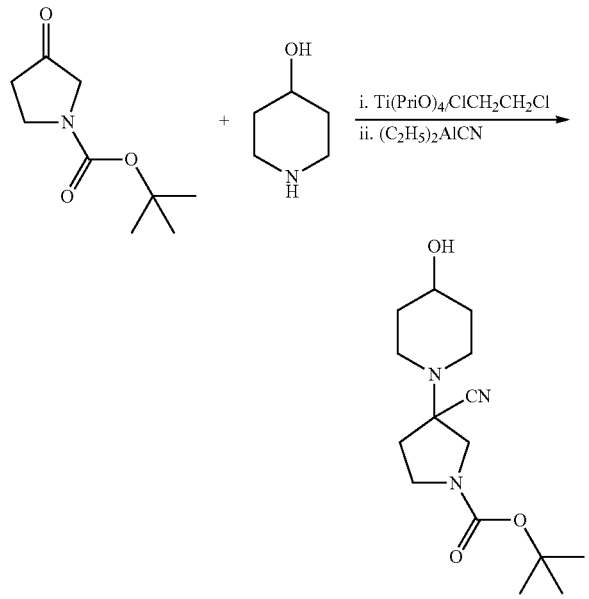

Following the procedure used in step A of the example 7 and starting with 4-hydroxypiperidine (5.0 g, 49.43 mmol) and tert-butyl 3-oxopyrrolidine-1-carboxylate (9.16 g, 49.43 mmol), the title compound was obtained as a white solid (5 g). MS (M+1): 296.19

Step B. The preparation of tert-butyl 3-(4-hydroxy-1-piperidyl)-3-methyl-pyrrolidine-1-carboxylate

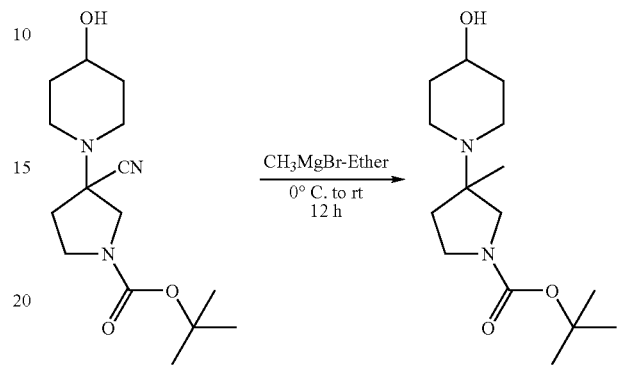

Following the procedure used in step B of the example 7 and starting with tert-butyl 3-cyano-3-(4-hydroxy-1-piperidyl)pyrrolidine-1-carboxylate (5.0 g, 16.93 mmol), the title compound was obtained as a white solid (3.5 g). MS (M+1): 285.19

Step C. The preparation of tert-butyl 3-methyl-3-(4-oxo-1-piperidyl)pyrrolidine-1-carboxylate

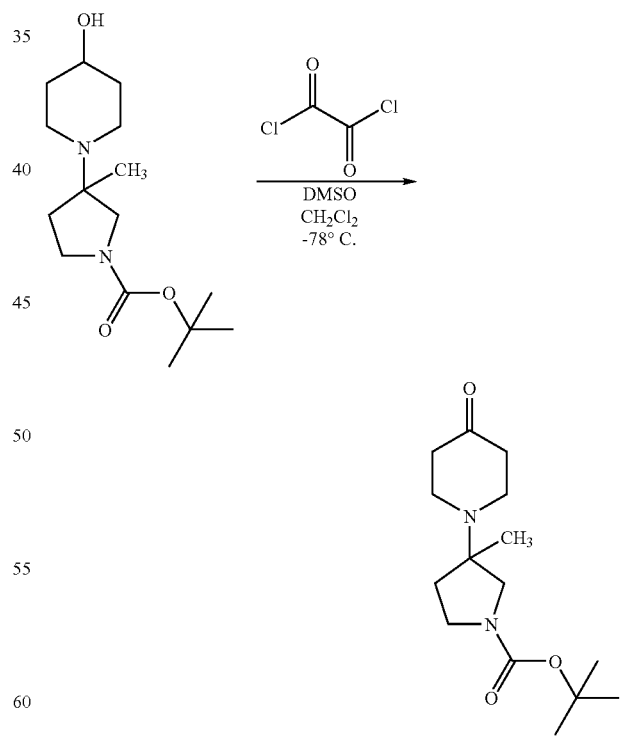

Following the procedure used in step C of the example 7 and starting with tert-butyl 3-(4-hydroxy-1-piperidyl)-3-methyl-pyrrolidine-1-carboxylate (3.5 g, 12.31 mmol), the title compound was obtained as a yellow solid (2.5 g). MS (M+1): 283.21

Step D. The preparation tert-butyl 3-[4-[[(1S,2S)-2-aminocyclohexyl]amino]-1-piperidyl]-3-methyl-pyrrolidine-1-carboxylate (mixture of diastereomers)

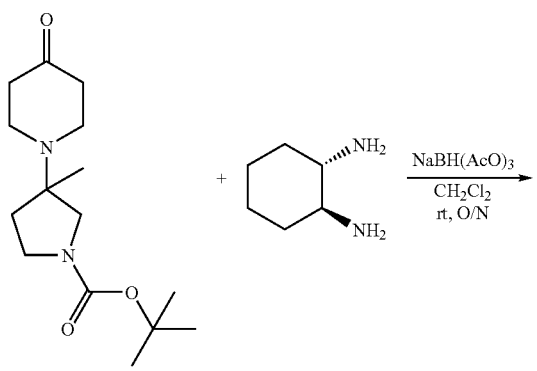

Following the procedure used in step D of the example 7 and starting with tert-butyl 3-methyl-3-(4-oxo-1-piperidyl)pyrrolidine-1-carboxylate (2.7 g, 9.56 mmol), the title compound was obtained as a white solid (2.5 g). MS (M+1): 381.30

Step E. The preparation of tert-butyl 3-[4-[(3aS,7aS)-2-oxo-3a,4,5,6,7,7a-hexahydro-3H-benzoimidazol-1-yl]-1-piperidyl]-3-methyl-pyrrolidine-1-carboxylate (mixture of diastereomers)

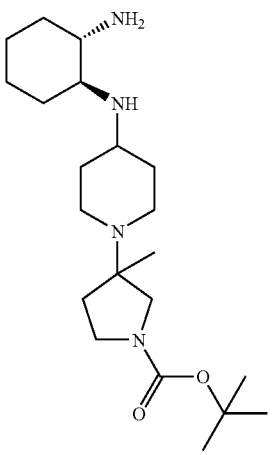

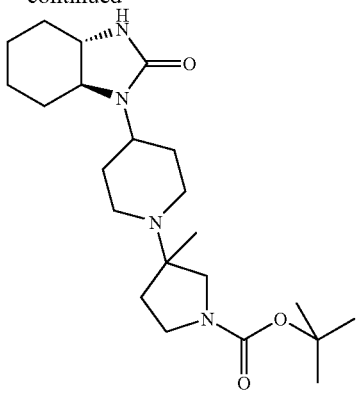

Following the procedure used in step E of the example 7 and starting with tert-butyl 3-[4-[[(1S,2S)-2-aminocyclohexyl]amino]-1-piperidyl]-3-methyl-pyrrolidine-1-carboxylate (2.5 g, 6.58 mmol), the title compound was obtained as a white solid (1.85 g). MS (M+1): 407.32

Step F. The preparation of (3aS,7aS)-1-[1-(3-methylpyrrolidin-3-yl)-4-piperidyl]-3a,4,5,6,7,7a-hexahydro-3H-benzoimidazol-2-one (mixture of diastereomers)

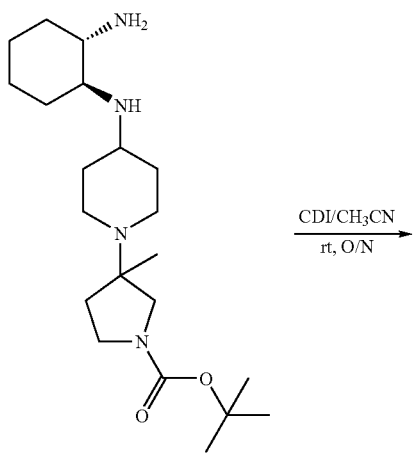

Tert-butyl 3-[4-[(3aS,7aS)-2-oxo-3a,4,5,6,7,7a-hexahydro-3H-benzoimidazol-1-yl]-1-piperidyl]-3-methyl-pyrrolidine-1-carboxylate (1.85 g, 4.55 mmol) in dioxane was added with 4N HCl solution in dioxane (11.4 mL, 45.5 mmol) and was stirred at room temperature under nitrogen atmosphere overnight. Then solvent was removed under reduced pressure to give the title compound as a white solid (1.3 g), which was used for the subsequent step without further purification. MS (M+1): 307.28.

Step G. The preparation of 2-fluoroethyl 3-[4-[(3aS,7aS)-2-oxo-3a,4,5,6,7,7a-hexahydro-3H-benzoimidazol-1-yl]-1-piperidyl]-3-methyl-pyrrolidine-1-carboxylate (mixture of diastereomers)

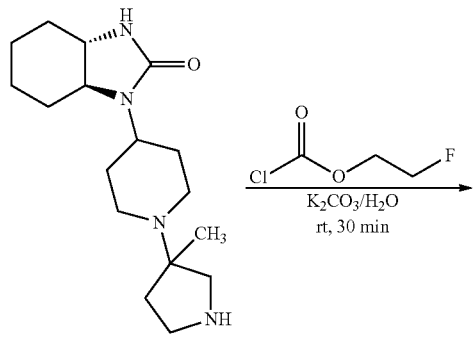

A solution of (3aS,7aS)-1-[1-(3-methylpyrrolidin-3-yl)-4-piperidyl]-3a,4,5,6,7,7a-hexahydro-3H-benzoimidazol-2-one (1 mmol) in water (10 mL) was added with potassium carbonate (4.0 equiv.) followed by 2-fluoroethyl chloroformate (1.2 equiv.) at room temperature and stirred at rt for 30 minutes. Extracted in ethyl acetate (2×10 mL), the combined organic layers were washed with brine, dried over anhydrous sodium sulfate and concentrated in vacuo. The crude product was purified by flash chromatography by eluting with methanol in ethyl acetate (0 to 5%) to afford the title compound (93 mg). $^1$H NMR (CD$_3$OD, 400 MHz): δ 4.65 (t, 2H), 4.53 (t, 1H), 4.34 (m, 1H), 4.27 (m, 1H), 3.62 (m, 3H), 3.48-3.37 (m, 2H), 3.25 (t, 1H), 3.03-2.90 (m, 3H), 2.77 (br t, 1H), 2.47 (m, 3H), 1.98-1.60 (br m, 9H), 1.43 (m, 3H), 1.11 (s, 3H); MS (M+1): 397.30.

Example 9

Prop-2-ynyl 3-[4-[(3aS,7aS)-2-oxo-3a,4,5,6,7,7a-hexahydro-3H-benzoimidazol-1-yl]-1-piperidyl]-3-methyl-pyrrolidine-1-carboxylate (mixture of diastereomers)

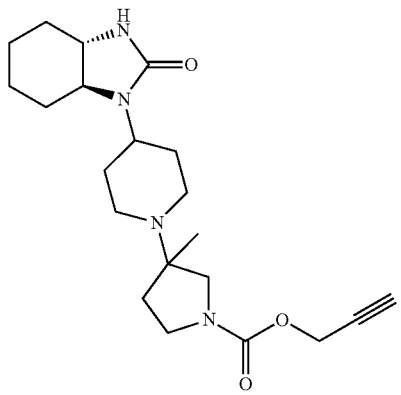

Following the procedure used in step G of the example 8 and using prop-2-ynyl chloroformate, the title compound was obtained as a white solid (107.2 mg). $^1$H NMR (CD$_3$OD, 400 MHz): δ 4.76 (d, 1H), 4.68 (d, 1H), 4.63 (br s, 1H), 3.64-3.57 (m, 2H), 3.46-3.40 (m, 2H), 3.24 (t, 1H), 3.02-2.91 (m, 4H), 2.76-2.71 (m, 1H), 2.45-2.31 (m, 3H), 1.99-1.60 (br m, 9H), 1.43 (m, 4H), 1.11 (s, 3H). MS (M+1): 389.30.

Example 10

Methyl 3-[4-[(3aS,7aS)-2-oxo-3a,4,5,6,7,7a-hexahydro-3H-benzoimidazol-1-yl]-1-piperidyl]-3-methyl-pyrrolidine-1-carboxylate (mixture of diastereomers)

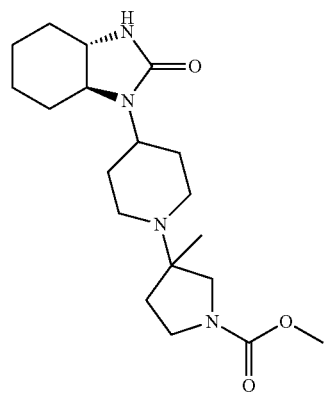

Following the procedure used in step G of the example 8 and using methyl chloroformate, the title compound was obtained as a white solid (100 mg). $^1$H NMR (CD$_3$OD, 400 MHz): δ d 4.63 (br s, 1H), 3.70-3.54 (m, 2H), 3.68 (s, 3H), 3.43-3.34 (m, 2H), 3.20 (d, 1H), 3.05-2.90 (m, 3H), 2.74-2.72 (m, 1H), 2.43-2.31 (m, 3H), 1.98-1.63 (m, 9H), 1.49 (m, 4H), 1.09 (s, 3H); MS (M+1): 365.30.

Example 11

Ethyl 3-[4-[(3aR,7aR)-2-oxo-3a,4,5,6,7,7a-hexahydro-3H-benzoimidazol-1-yl]-1-piperidyl]-3-methyl-pyrrolidine-1-carboxylate (mixture of diastereomers)

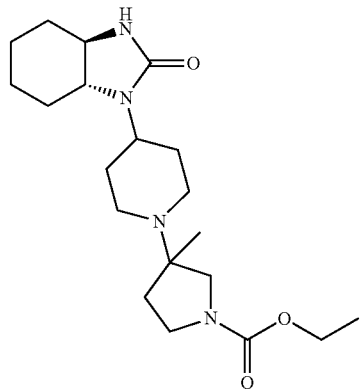

47

Step A. The preparation tert-butyl 3-[4-[[(1R,2R)-2-aminocyclohexyl]amino]-1-piperidyl]-3-methyl-pyrrolidine-1-carboxylate (mixture of diastereomers)

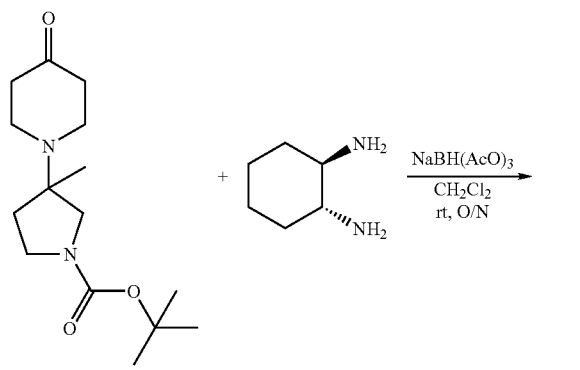

Following the procedure used in step D of the example 7 and starting with tert-butyl 3-methyl-3-(4-oxo-1-piperidyl)pyrrolidine-1-carboxylate (300 mg, 1.06 mmol) and 1R,2R-diaminocyclohexane (244.2 mg, 2.12 mmol), the title compound was obtained (300 mg). MS (M+1): 381.30

Step B. The preparation of tert-butyl 3-[4-[(3aR,7aR)-2-oxo-3a,4,5,6,7,7a-hexahydro-3H-benzoimidazol-1-yl]-1-piperidyl]-3-methyl-pyrrolidine-1-carboxylate (mixture of diastereomers)

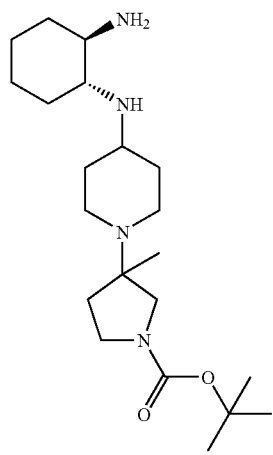

48

-continued

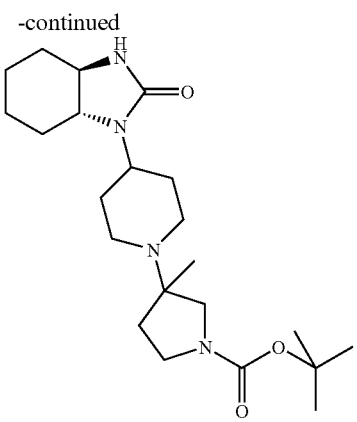

Following the procedure used in step E of the example 7 and starting with tert-butyl 3-[4-[[(1R,2R)-2-aminocyclohexyl]amino]-1-piperidyl]-3-methyl-pyrrolidine-1-carboxylate (300 mg, 0.79 mmol), the title compound (200 mg) was obtained. $^1$H NMR (CDCl$_3$): δ 4.40 (s, 1H), 3.78-3.66 (m, 2H), 3.55-3.27 (m, 3H), 3.13 (t, 1H), 3.00 (br s, 2H), 2.82 (br m, 1H), 2.66 (br m, 1H), 2.40-2.29 (m, 3H), 1.97 (br d, 1H), 1.82-1.68 (br m, 9H), 1.45 (s, 9H), 1.45-1.25 (m, 2H), 1.04 (s, 3H).

Step C. The preparation of (3aR,7aR)-1-[1-(3-methylpyrrolidin-3-yl)-4-piperidyl]-3a,4,5,6,7,7a-hexahydro-3H-benzoimidazol-2-one (mixture of diastereomers)

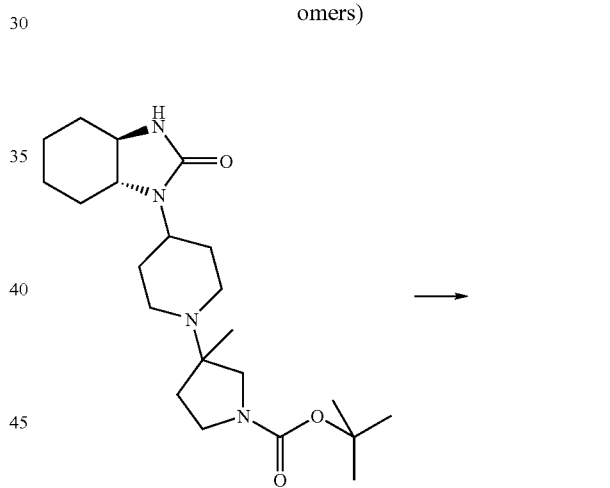

Following the procedure used in step F of the example 8 and starting with tert-butyl 3-[4-[(3aR,7aR)-2-oxo-3a,4,5,6,7,7a-hexahydro-3H-benzoimidazol-1-yl]-1-piperidyl]-3-methyl-pyrrolidine-1-carboxylate (200 mg, 0.492 mmol), the title compound was obtained as a white solid (160 mg) and used for the subsequent step without further purification. MS (M+1): 307.28.

Step D. The preparation of Ethyl 3-[4-[(3aR,7aR)-2-oxo-3a,4,5,6,7,7a-hexahydro-3H-benzoimidazol-1-yl]-1-piperidyl]-3-methyl-pyrrolidine-1-carboxylate (mixture of diastereomers)

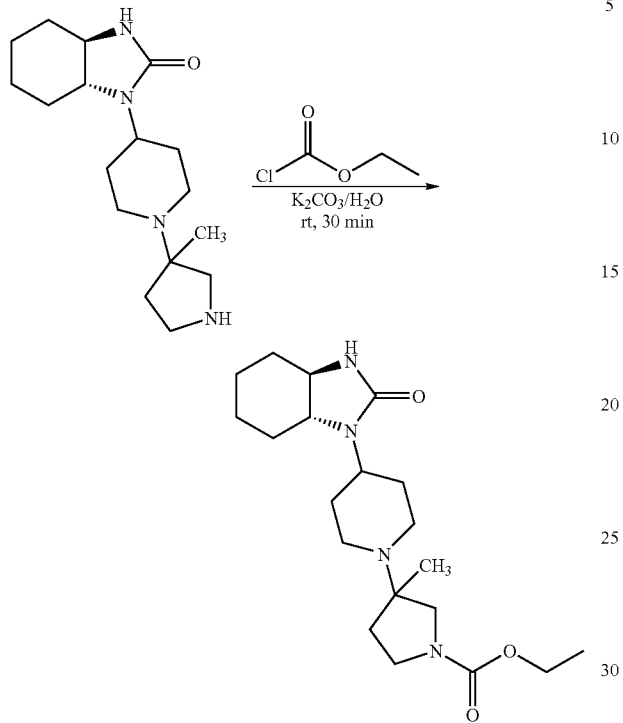

Following the procedure used in step G of the example 8 and starting with (3aR,7aR)-1-[1-(3-methylpyrrolidin-3-yl)-4-piperidyl]-3a,4,5,6,7,7a-hexahydro-3H-benzoimidazol-2-one (160 mg, 0.522 mmol) and ethyl chloroformate (85 mg, 0.783 mmol), the title compound was obtained as a gum (120 mg). $^1$H NMR (Methanol-D4) δ 4.60 (brs, 1H), 4.13-4.08 (q, 2H), 3.74-3.51 (m, 4H), 3.43-3.34 (m, 2H), 3.20 (br d, 1H), 3.04-2.90 (m, 3H), 2.73 (br s, 1H), 2.4-2.31 (m, 3H), 1.98-1.60 (br m, 8H), 1.43 (m, 3H), 1.25 (t, 3H), 1.10 (s, 3H). MS (M+1): 379.34.

Example 12

Ethyl 4-[4-[(cis)-2-oxo-3a,4,5,6,7,7a-hexahydro-3H-benzoimidazol-1-yl]-1-piperidyl]-4-methyl-piperidine-1-carboxylate

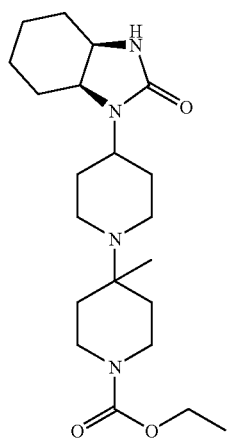

Step A. The preparation of tert-butyl 4-[4-[[(cis)-2-aminocyclohexyl]amino]-1-piperidyl]-4-methyl-piperidine-1-carboxylate

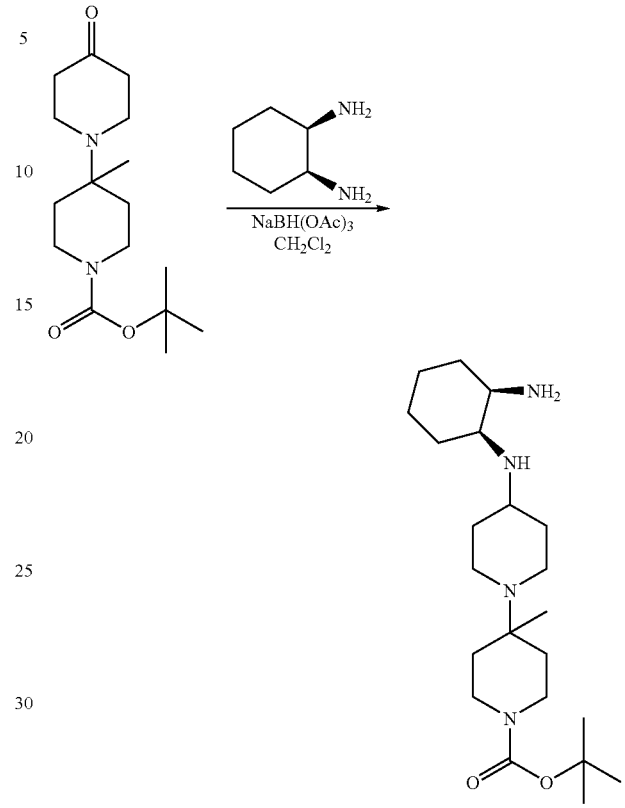

To a solution of cis-cyclohexane-1,2-diamine (0.850 mL, 7.22 mmol) in dichloromethane (10 mL) was added with tert-butyl 4-methyl-4-(4-oxo-1-piperidyl)piperidine-1-carboxylate (1.39 g, 3.61 mmol) in dichloromethane (5 mL) followed by sodium triacetoxyborohydride (0.918 g, 4.33 mmol) and the mixture stirred at room temperature over night. The mixture was then quenched with 1 N NaOH and dichloromethane was added. The phases were separated and aqueous phase was extracted with dichloromethane. The combined organic phases were dried and concentrated in vacuo to give the title product, which was used for the subsequent step without further purification. MS (M+1): 395.37.

Step B. The preparation of tert-butyl 4-[4-[(cis)-2-oxo-3a,4,5,6,7,7a-hexahydro-3H-benzoimidazol-1-yl]-1-piperidyl]-4-methyl-piperidine-1-carboxylate

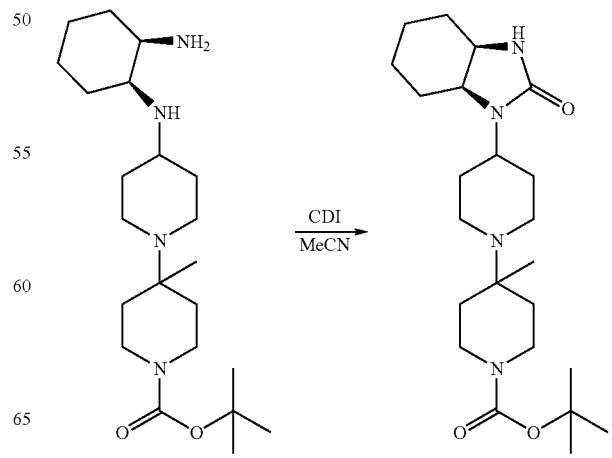

To a solution of tert-butyl 4-[4-[[(cis)-2-aminocyclohexyl]amino]-1-piperidyl]-4-methyl-piperidine-1-carboxylate (1.4 g, 3.55 mmol) in acetonitrile (30 mL) was added 1,1-carbonyldiimidazole (0.575 g, 3.55 mmol) and the mixture was stirred at room temperature over night. Concentrated in vacuo and the residue was diluted with dichloromethane. A solution of 1N NaOH was then added, the aqueous phase was separated and extracted with dichloromethane. The combined organic phases were dried and concentrated in vacuo. The crude product was purified by flash chromatography (MeOH/Dichloromethane gradient) to provide the title compound (1.4 g), which was used for the subsequent step without further purification. MS (M+1): 421.38.

Step C. The preparation of (cis)-1-[1-(4-methyl-4-piperidyl)-4-piperidyl]-3a,4,5,6,7,7a-hexahydro-3H-benzoimidazol-2-one

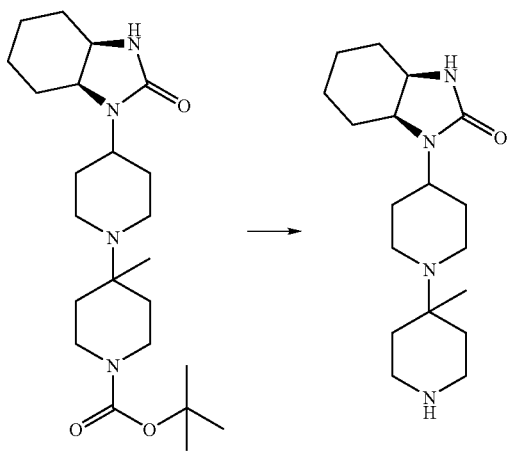

To a solution of (cis)-1-[1-(4-methyl-4-piperidyl)-4-piperidyl]-3a,4,5,6,7,7a-hexahydro-3H-benzoimidazol-2-one (1.4 g, 3.33 mmol) in methanol (25 mL) was added 4M solution of hydrochloric acid (10 mL, 40.00 mmol) in dioxane and the mixture was stirred at room temperature over night. Concentrated in vacuo to give the title compound as a white solid (1.4 g), which was used for the subsequent step without further purification. MS (M+1): 321.31.

Step D. The preparation of ethyl 4-[4-[(cis)-2-oxo-3a,4,5,6,7,7a-hexahydro-3H-benzoimidazol-1-yl]-1-piperidyl]-4-methyl-piperidine-1-carboxylate

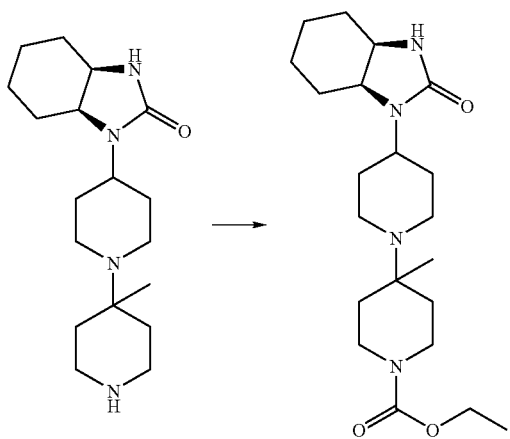

To a solution of crude (cis)-1-[1-(4-methyl-4-piperidyl)-4-piperidyl]-3a,4,5,6,7,7a-hexahydro-3H-benzoimidazol-2-one (HCl salt, 0.3 g) in dichloromethane (10 mL) was added diisopropylethyl amine (0.337 g, 2.61 mmol) followed by a solution of ethyl chloroformate (0.119 g, 1.09 mmol) in dichloromethane (1 mL) dropwise over 30 minutes at 0° C. and the mixture stirred at this temperature for 2 h. The mixture was then quenched by ice and diluted with dichloromethane and aqueous phase was extracted with dichloromethane. The combined organic phases were dried and concentrated in vacuo. The residue was then purified by preparative LC/MS (high pH) to provide the title compound as an off white solid (60 mg, 18%). $^1$H NMR (400 MHz, CHLOROFORM-D) δ ppm 0.88 (s, 3H), 1.07-1.21 (m, 1H), 1.23 (t, J=7.03 Hz, 3H), 1.29-1.43 (m, 3H), 1.45-1.92 (m, 13H), 2.02-2.24 (m, 2H), 2.81-3.01 (m, 2H), 3.23-3.40 (m, 2H), 3.41-3.69 (m, 5H), 4.10 (q, J=7.29 Hz, 2H).

MS (M+1): 393.28.

Example 13

Propan-2-yl 4-[4-[(cis)-2-oxo-3a,4,5,6,7,7a-hexahydro-3H-benzoimidazol-1-yl]-1-piperidyl]-4-methyl-piperidine-1-carboxylate

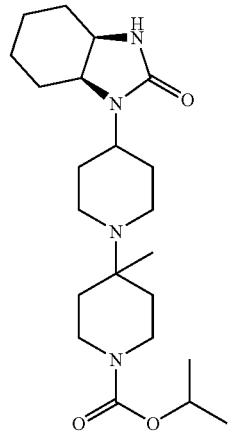

To a solution of (cis)-1-[1-(4-methyl-4-piperidyl)-4-piperidyl]-3a,4,5,6,7,7a-hexahydro-3H-benzoimidazol-2-one (HCl salt, 0.3 g, 0.76 mmol) in dichloromethane (10 mL) at 0° C. was added diisopropylethyl amine (0.315 g, 2.44 mmol) followed by isopropyl chloroformate (0.112 g, 0.92 mmol) dropwise over 30 minutes and stirred at 0° C. for 2 hours. The reaction was quenched with 1N NaOH and aqueous phase extracted with dichloromethane. The combined organic phases were dried and concentrated in vacuo. The residue was then purified by using preparative LC/MS (high pH) to provide the title compound (127 mg, 41%). 1H NMR (400 MHz, CHLOROFORM-D) δ ppm 0.86 (s, 3H), 1.06-1.18 (m, 1H), 1.20 (d, J=6.25 Hz, 6H), 1.27-1.42 (m, 3H), 1.44-1.90 (m, 12H), 1.98-2.26 (m, 2H), 2.77-2.99 (m, 2H), 3.20-3.39 (m, 2H), 3.40-3.72 (m, 5H), 4.16-4.36 (m, 1H), 4.72-4.92 (m, 1H). MS (M+1): 407.30.

Example 14

Propan-2-yl 4-[4-[(3aR,7aS)-2-oxo-3a,4,5,6,7,7a-hexahydro-3H-indol-1-yl]-1-piperidyl]-4-methyl-piperidine-1-carboxylate

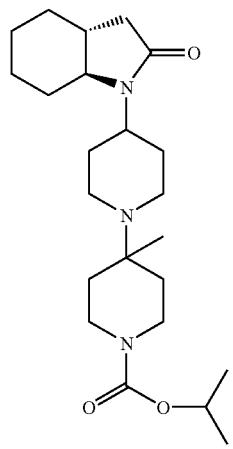

Step A. The preparation of tert-butyl N-[(1S,2S)-2-(methylsulfonyloxymethyl)cyclohexyl]carbamate

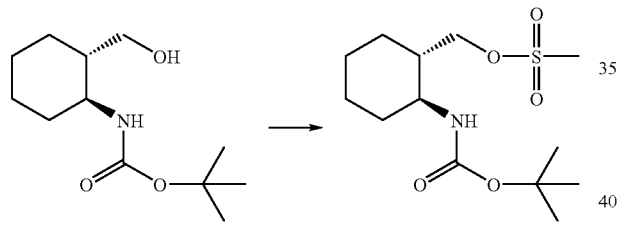

A solution of tert-butyl N-[(1S,2S)-2-(hydroxymethyl)cyclohexyl]carbamate (1.3 g, 5.68 mmol) in dichloromethane (10 mL) was added drop wise with methane sulfonyl chloride (0.52 mL, 6.75 mmol) at 0° C. Triethylamine (1 mL) was then added and the mixture stirred for 2 hours. The reaction mixture was quenched with ice and diluted in dichloromethane. Washed with a saturated solution of NaHCO₃ and brine, dried and concentrated in vacuo to provide the title compound as brown solid (1.8 g). MS (M+1): 308.16

Step B. The preparation of tert-butyl N-[(1S,2R)-2-(cyanomethyl)cyclohexyl]carbamate

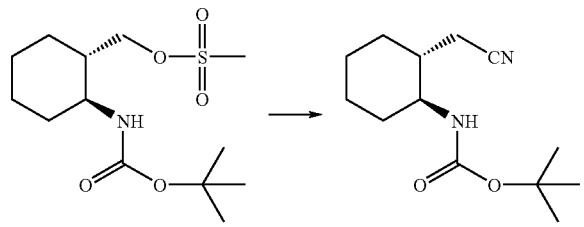

A solution of tert-butyl N-[(1S,2S)-2-(methylsulfonyloxymethyl)cyclohexyl]carbamate (1.8 g) in dry DMSO was added with potassium cyanide (0.52 g, 7.76 mL) and the mixture was then heated at 90° C. under N₂ for 4 hours. The mixture was cooled and then poured on to water (50 mL) and extracted with ether (3×30 mL). The combined organic phases were washed with brine and concentrated in vacuo to provide the title compound.

Step C. The preparation of 2-[(1R,2S)-2-aminocyclohexyl]acetonitrile

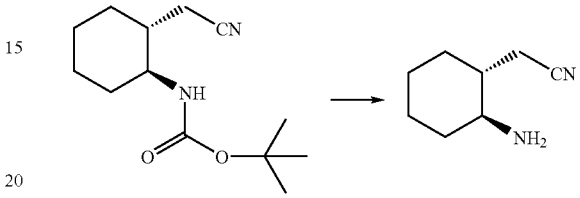

A solution tert-butyl N-[(1S,2R)-2-(cyanomethyl)cyclohexyl]carbamate (2 g) in MeOH (40 mL) and 4 M HCl in dioxane (20 mL) was stirred at room temperature for 2 hours and concentrated in vacuo to provide the title compound as a yellow oil, which was used for the subsequent step without further purification.

Step D. The preparation tert-butyl 4-[4-[[(1S,2R)-2-(cyanomethyl)cyclohexyl]amino]-1-piperidyl]-4-methyl-piperidine-1-carboxylate

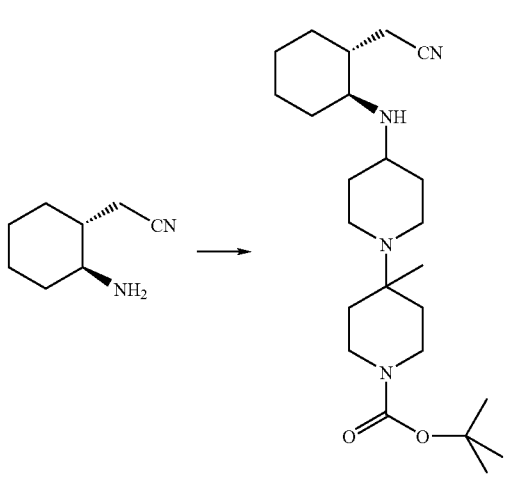

To a solution 2-[(1R,2S)-2-aminocyclohexyl]acetonitrile (HCl salt, 0.7 g, 3.32 mmol) in MeOH (10 mL) was added triethylamine (0.48 mL, 3.47 mmol) followed of tert-butyl 4-methyl-4-(4-oxo-1-piperidyl)piperidine-1-carboxylate (1 g, 3.38 mmol) at room temperature. A solution containing sodium cyanoborohydride (0.34 g, 4.93 mmol) and zinc(II) chloride (0.22 g, 1.62 mmol) in MeOH (2 mL) was then added dropwise and the mixture stirred at room temperature overnight. Concentrated in vacuo, the residue was diluted in dichloromethane (100 mL) and washed with 1N NaOH (10 mL). The aqueous phase was separated and was extracted with dichloromethane (2×20 mL). The combined organic phase was washed with brine and concentrated in vacuo to provide the title compound, which was used for the next step without any purification. MS (M+1): 419.37.

Step E. The preparation of 2-[(1R,2S)-2-[[1-[4-methyl-1-[(2-methylpropan-2-yl)oxycarbonyl]-4-piperidyl]-4-piperidyl]amino]cyclohexyl]acetic acid

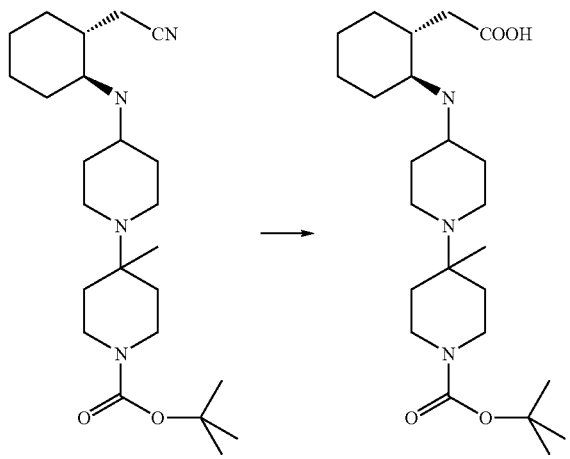

A solution of tert-butyl 4-[4-[[(1S,2R)-2-(cyanomethyl)cyclohexyl]amino]-1-piperidyl]-4-methyl-piperidine-1-carboxylate in EtOH (30 mL) and 2N aqueous NaOH (10 mL) was heated at reflux overnight. Additional amount of 2N NaOH (12 mL) was then added and the concentrated in vacuo. The residue acidified (pH 3-4) with 1 N HCl and concentrated in vacuo. The solid residue was washed with MeOH, filtered and the filtrate concentrated in vacuo to provide the title compound, which was used for the subsequent step without further purification. MS (M+1): 438.42.

Step F. The preparation tert-butyl 4-[4-[(3aR,7aS)-2-oxo-3a,4,5,6,7,7a-hexahydro-3H-indol-1-yl]-1-piperidyl]-4-methyl-piperidine-1-carboxylate

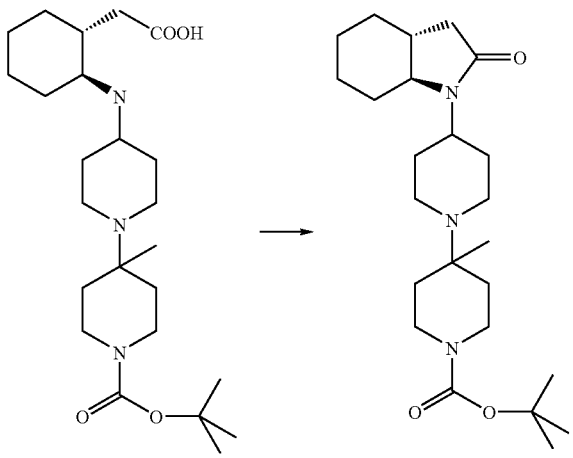

A solution of 2-[(1R,2S)-2-[[1-[4-methyl-1-[(2-methylpropan-2-yl)oxycarbonyl]-4-piperidyl]-4-piperidyl]amino]cyclohexyl]acetic acid, diisopropylethylamine (0.5 mL, 3.36 mmol) and HATU (0.7 g, 1.84 mmol) in DMF (10 mL) was stirred at room temperature overnight. The reaction quenched with water and concentrated in vacuo. The residue was diluted in ethylacetate (100 mL) and washed with 1N NaOH (10 mL). The organic phase was separated and aqueous phase was extracted with ethylacetate (2×30 mL). The combined organic phases were dried and concentrated in vacuo to provide the title compound. MS (M+1): 420.38.

Step G. The preparation of (3aR,7aS)-1-[1-(4-methyl-4-piperidyl)-4-piperidyl]-3a,4,5,6,7,7a-hexahydro-3H-indol-2-one

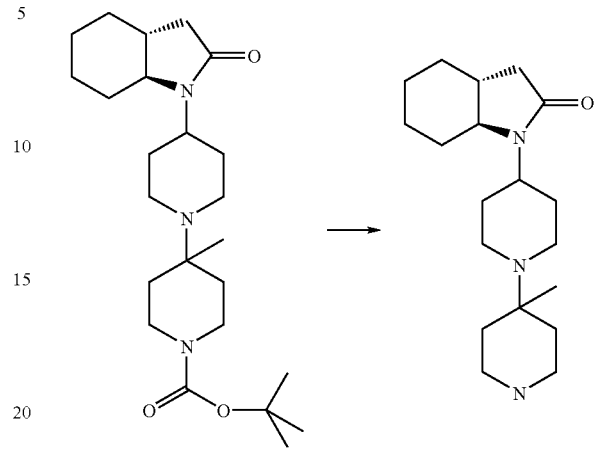

A solution of tert-butyl 4-[4-[(3aR,7aS)-2-oxo-3a,4,5,6,7,7a-hexahydro-3H-indol-1-yl]-1-piperidyl]-4-methyl-piperidine-1-carboxylate in MeOH (14 mL) and 4M HCl in dioxane (5 mL) was stirred at room temperature overnight. Concentrated in vacuo and the residue was purified by preparative LC/MS (high pH) to provide the title compound as a colorless oil (0.41 g). MS (M+1): 320.30.

Step H. The tert-butyl 4-[4-[(3aR,7aS)-2-oxo-3a,4,5,6,7,7a-hexahydro-3H-indol-1-yl]-1-piperidyl]-4-methyl-piperidine-1-carboxylate

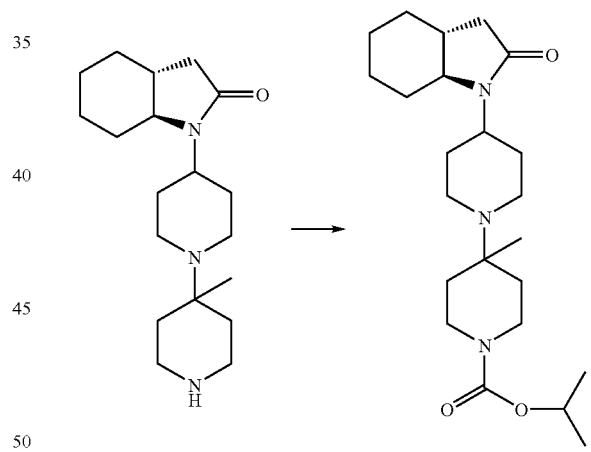

A solution of (3aR,7aS)-1-[1-(4-methyl-4-piperidyl)-4-piperidyl]-3a,4,5,6,7,7a-hexahydro-3H-indol-2-one (100 mg, 0.31 mmol) and triethylamine (0.044 mL, 0.31 mmol) in dichloromethane (5 mL) was added with isopropyl chloroformate (0.313 mL, 1M solution in toluene, 0.31 mmol) dropwise at 0° C. and stirred for 2 hours. Diluted with dichloromethane (60 mL) and 1 N NaOH (10 mL) was added. The phases were separated and aqueous phase was extracted with dichloromethane (2×15 mL). The combined organic phases were washed with brine, concentrated in vacuo and the residue was purified by preparative LC/MS (high pH) to provide the title compound (63 mg, 49.6%). $^1$H NMR (400 MHz, CHLOROFORM-D) δ ppm 0.85 (s, 3H), 1.19 (d, J=6.25 Hz, 6H), 1.21-1.43 (m, 6H), 1.48-1.87 (m, 10H), 1.87-2.00 (m, 1H), 2.04-2.18 (m, 2H), 2.28 (d, J=6.64 Hz, 1H), 2.32 (d, J=7.03 Hz, 1H), 2.88 (t, J=12.70 Hz, 2H), 2.97 (t, J=8.59 Hz, 1H), 3.20-3.35 (m, 2H), 3.39-3.58 (m, 2H), 3.90 (t, J=12.30 Hz, 1H), 4.76-4.93 (m, 1H). MS (M+1): 406.2.

Example 15

(3aR,7aS)-1-[1-[1-(cyclopropanecarbonyl)-4-methyl-4-piperidyl]-4-piperidyl]-3a,4,5,6,7,7a-hexahydro-3H-indol-2-one

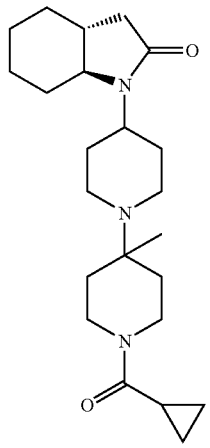

A solution of (3aR,7aS)-1-[1-(4-methyl-4-piperidyl)-4-piperidyl]-3a,4,5,6,7,7a-hexahydro-3H-indol-2-one (70 mg, 0.22 mmol) in DMF (3 mL) was added with cyclopropane carboxylic acid (18.86 mg, 0.22 mmol) and diisopropylethyl amine (0.046 mL, 0.26 mmol) at room temperature. After 5-10 minutes HATU (83 mg, 0.22 mmol) was added and the mixture stirred at room temperature over night. The solvent was removed in vacuo, the residue dissolved in dichloromethane (60 mL) and washed with 1N NaOH (7 mL) and brine and concentrated in vacuo. The residue was purified by preparative LC/MS (high pH) to provide the title compound (58 mg, 69%). $^1$H NMR (400 MHz, CHLOROFORM-D) δ ppm 0.54-0.74 (m, 2H), 0.77-0.95 (m, 2H), 0.84 (s, 3H), 1.01-1.44 (m, 6H), 1.45-1.84 (m, 11H), 2.01-2.15 (m, 2H), 2.19-2.40 (m, 2H), 2.73-3.06 (m, 3H), 3.17-3.32 (m, 1H), 3.37 (s, 1H), 3.44-3.68 (m, 2H), 3.69-3.80 (m, 1H), 3.81-3.97 (m, 1H). MS (M+1): 388.3.

Example 16

But-2-ynyl 4-[4-[(3aS,7aS)-2-oxo-3a,4,5,6,7,7a-hexahydro-3H-benzimidazol-1-yl]-1-piperidyl]-4-methyl-piperidine-1-carboxylate

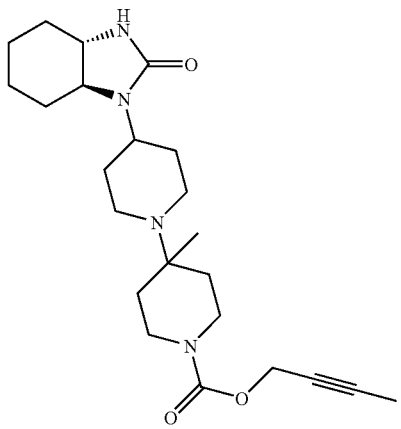

To a solution of (3aS,7aS)-3-[1-(4-methyl-4-piperidyl)-4-piperidyl]-3a,4,5,6,7,7a-hexahydro-1H-benzimidazol-2-one (HCl salt, 0.4105 g, 1.15 mmol) and potassium carbonate (0.170 g, 1.23 mmol) in water (3.00 mL) was added a solution of but-2-ynyl chloroformate (0.156 mL, 1.38 mmol) in dichloromethane (3 mL). The reaction mixture was stirred at room temperature overnight. The mixture was poured into hydrometrix varian column chem elut catridge column and rinsed with dichloromethane (3 Column volumes). Concentrated in vacuo and the residue was purified by flash chromatography (0 to 50% MeOH/Ethyl acetate) and followed by preparative LC/MS (high pH) to give the title compound (0.036 g, 7.59%). $^1$H NMR (400 MHz, CHLOROFORM-D) δ ppm 1H NMR (400 MHz, CDCl$_3$) δ ppm 1.30-1.47 (m, 6H), 1.49 (s, 2H), 1.62-1.76 (m, 1H), 1.76-2.00 (m, 9H), 2.34 (s, 2H), 2.72-2.98 (m, 6H), 2.99-3.09 (m, 2H), 3.49-3.85 (m, 2H), 4.11 (s, 1H), 4.27 (s, 2H), 4.49 (s, 1H), 4.61-4.72 (m, 2H) MS (M+1): 417.3.

Example 17 prop-2-ynyl 4-[4-[(3aS,7aS)-2-oxo-3a,4,5,6,7,7a-hexahydro-3H-benzimidazol-1-yl]-1-piperidyl]-4-methyl-piperidine-1-carboxylate

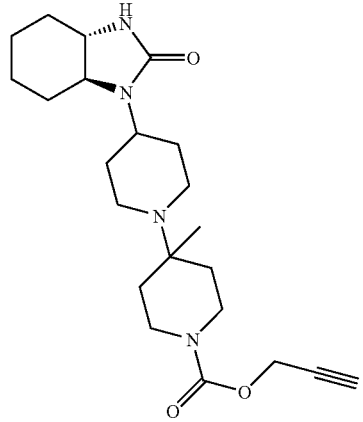

Following the procedure used in example 16 and starting from (3aS,7aS)-3-[1-(4-methyl-4-piperidyl)-4-piperidyl]-3a,4,5,6,7,7a-hexahydro-1H-benzimidazol-2-one (HCl salt, 181 mg, 0.51 mmol) and prop-2-ynyl chloroformate (0.050 mL, 0.51 mmol), the title compound (19.40 mg, 9.50%) was obtained after purification by preparative LC/MS (high pH). $^1$H NMR (400 MHz, CHLOROFORM-D) δ ppm 1.29-1.47 (m, 5H), 1.49 (s, 3H), 1.76-2.01 (m, 8H), 2.29-2.44 (m, 2H), 2.82 (t, J=9.96 Hz, 5H), 2.90 (d, J=10.55 Hz, 2H), 3.03 (d, J=6.64 Hz, 1H), 3.68 (t, J=9.57 Hz, 2H), 4.06-4.17 (m, 1H), 4.27 (d, J=19.53 Hz, 2H), 4.52 (s, 1H), 4.69 (s, 1H), 4.76 (s, 1H). MS (M+1): 403.3.

Example 18

(3aS,7aS)-3-[1-(4-methyl-1-propanoyl-4-piperidyl)-4-piperidyl]-3a,4,5,6,7,7a-hexahydro-1H-benzimidazol-2-one

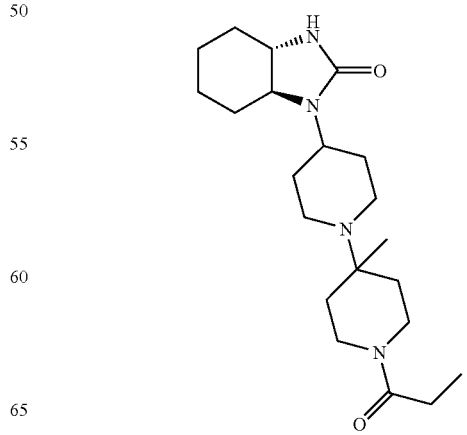

Following the procedure used in Step H of example 14 and starting from (3aS,7aS)-3-[1-(4-methyl-4-piperidyl)-4-piperidyl]-3a,4,5,6,7,7a-hexahydro-1H-benzimidazol-2-one (HCl salt, 1.5 g, 3.8 mmol) and propanoyl chloride (0.43 mL, 4.89 mmol), the title compound (740 mg, 51.7%) was obtained after purification by flash chromatography (4% MeOH in dichloromethane). $^1$H NMR (400 MHz, CHLOROFORM-D) δ ppm 0.96 (s, 3H), 1.18 (t, 3H), 1.3-1.5 (m, 6H), 1.4-1.9 (m, 8H), 1.92-2.02 (m, 1H), 2.1-2.3 (m, 3H), 2.32-2.4 (m, 2H), 2.84-3.08 (m, 4H), 3.23-3.4 (m, 2H), 3.42-3.5 (m, 1H), 3.82-3.88 (m, 1H), 3.7-3.8 (m, 1H), 4.43 (s, 1H). MS (M+1): 377.16

Example 19 (Diastereomer 1) and Example 20 (Diastereomer 2)

But-2-ynyl 3-[4-[(3aS,7aS)-2-oxo-3a,4,5,6,7,7a-hexahydro-3H-benzimidazol-1-yl]-1-piperidyl]-3-methyl-pyrrolidine-1-carboxylate

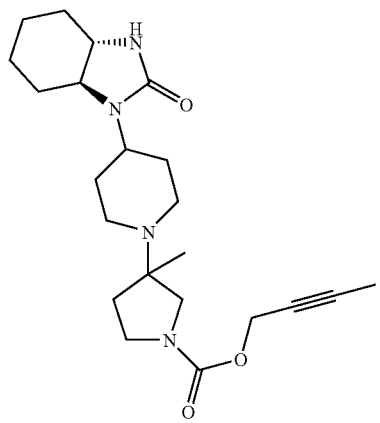

Diastereomer 1

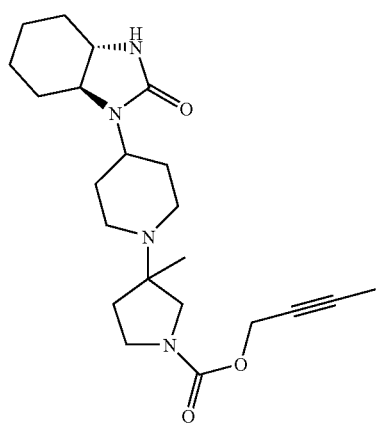

Diastereomer 2

Step A: The preparation of but-2-ynyl 3-[4-[(3aS,7aS)-2-oxo-3a,4,5,6,7,7a-hexahydro-3H-benzimidazol-1-yl]-1-piperidyl]-3-methyl-pyrrolidine-1-carboxylate (mixture of diastereomers)

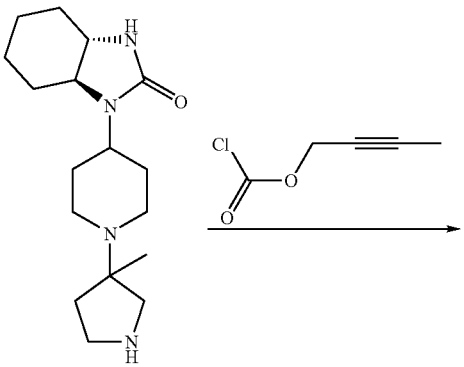

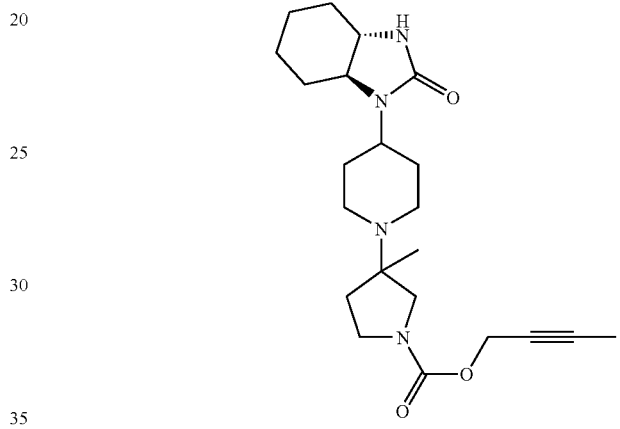

Following the procedure used in example 16 and starting from (3aS,7aS)-3-[1-(3-methylpyrrolidin-3-yl)-4-piperidyl]-3a,4,5,6,7,7a-hexahydro-1H-benzimidazol-2-one (HCl salt, 0.6 g, 1.75 mmol) and but-2-ynyl chloroformate (0.218 mL, 1.92 mmol), the title compound (0.239 g, 33.9%) was obtained after purification by preparative LC/MS (high pH) as a mixture of diastereomers. MS (M+1): 403.3

Step B: Separation of diastereomers of but-2-ynyl 3-[4-[(3aS,7aS)-2-oxo-3a,4,5,6,7,7a-hexahydro-3H-benzimidazol-1-yl]-1-piperidyl]-3-methyl-pyrrolidine-1-carboxylate

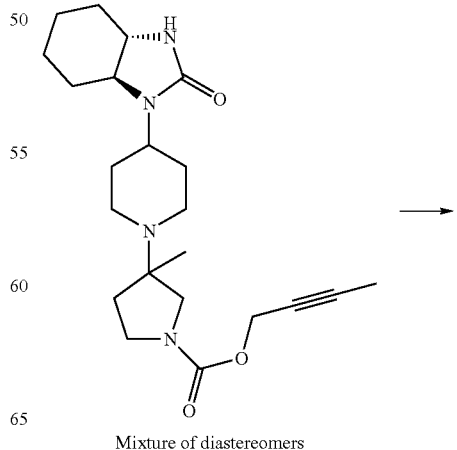

Mixture of diastereomers

-continued

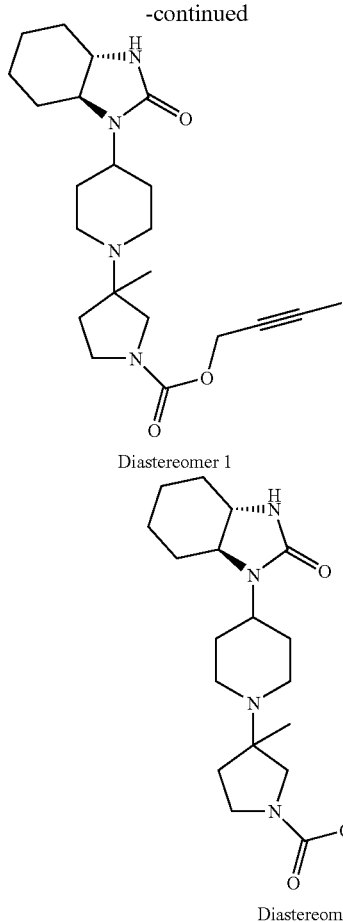

Diastereomer 1

Diastereomer 2

Mixture of diastereomers of but-2-ynyl 3-[4-[(3aS,7aS)-2-oxo-3a,4,5,6,7,7a-hexahydro-3H-benzimidazol-1-yl]-1-piperidyl]-3-methyl-pyrrolidine-1-carboxylate (0.220 g, 0.55 mmol) was separated supercritical fluid chromatography (OJ chiral column, Eluents: 10% EtOH+0.1% dimethylethylamine and CO$_2$ as main eluent) to give Diastereomer 1 and Diastereomer 2 of but-2-ynyl 3-[4-[(3aS,7aS)-2-oxo-3a,4,5,6,7,7a-hexahydro-3H-benzimidazol-1-yl]-1-piperidyl]-3-methyl-pyrrolidine-1-carboxylate.

Diastereomer 1 (Example 19): (0.083 g), Retention time: 2.21 minutes (Supercritical fluid chromatography, Chiral OJ Column, Eluents: 20% EtOH+dimethylethylamine and CO$_2$ as main eluent, room temperature) $^1$H NMR (400 MHz, CHLOROFORM-D) δ ppm 1.37 (s, 7H), 1.71-1.83 (m, 3H), 1.84 (d, J=1.95 Hz, 3H), 1.88-2.01 (m, 3H), 2.19-2.45 (m, 1H), 2.66 (d, J=12.50 Hz, 1H), 2.70-2.89 (m, 2H), 2.89-3.13 (m, 5H), 3.26-3.35 (m, 1H), 3.45 (dd, J=7.03 Hz, 2H), 3.59 (dd, J=30.47, 9.37 Hz, 1H), 3.67-3.84 (m, 1H), 4.01-4.19 (m, 1H), 4.50 (s, 1H), 4.65 (s, 2H). MS (M+1): 403.3

Diastereomer 2 (Example 20): (0.093 g), Retention time: 2.55 minutes (Supercritical fluid chromatography, Chiral OJ Column, Eluents: 20% EtOH+dimethylethylamine and CO$_2$ as main eluent, room temperature). $^1$H NMR (400 MHz, CHLOROFORM-D) δ ppm 1.27-1.44 (m, 7H), 1.68-1.91 (m, 6H), 1.90-1.98 (m, 3H), 2.39-2.70 (m, 3H), 2.78 (d, J=3.91 Hz, 1H), 2.81-2.96 (m, 1H), 3.00 (d, J=6.64 Hz, 3H), 3.04-3.18 (m, 1H), 3.22-3.35 (m, 1H), 3.40-3.51 (m, 2H), 3.52-3.66 (m, 1H), 3.72 (t, J=9.57 Hz, 1H), 3.90-4.24 (m, 1H), 4.51 (s, 1H), 4.65 (s, 2H). MS (M+1): 403.3.

Example 21 (Diastereomer 1) and Example 22 (Diastereomer 2)

ethyl 3-[4-[(3aS,7aS)-2-oxo-3a,4,5,6,7,7a-hexahydro-3H-benzimidazol-1-yl]-1-piperidyl]-3-methyl-pyrrolidine-1-carboxylate

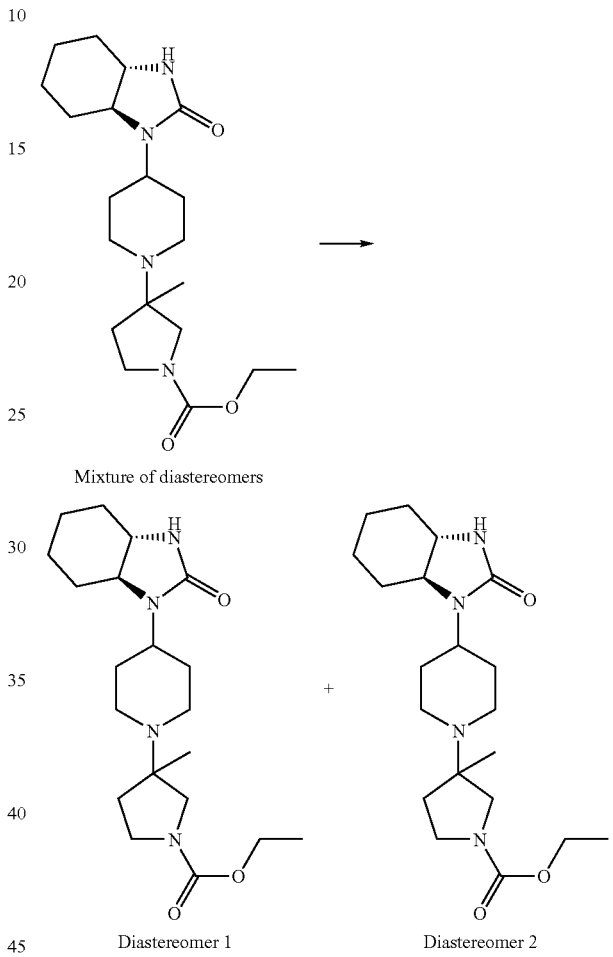

Diastereomers of ethyl 3-[4-[(3aS,7aS)-2-oxo-3a,4,5,6,7,7a-hexahydro-3H-benzimidazol-1-yl]-1-piperidyl]-3-methyl-pyrrolidine-1-carboxylate was separated by supercritical fluid chromatography (AD chiral column, column temperature 35° C., Eluents: 40% EtOH+0.1% dimethylethylamine and CO$_2$ as main eluent) to give Diastereomer 1 and Diastereomer 2 of ethyl 3-[4-[(3aS,7aS)-2-oxo-3a,4,5,6,7,7a-hexahydro-3H-benzimidazol-1-yl]-1-piperidyl]-3-methyl-pyrrolidine-1-carboxylate Diastereomer 1 (Example 21) was further purified by preparative LC/MS (Low pH). (0.300 g, 53.1%), Retention time: 3.37 minutes (Supercritical fluid chromatography, AD chiral column, column temperature 35° C., Eluents: 40% EtOH+0.1% dimethylethylamine and CO$_2$ as main eluent). $^1$H NMR (400 MHz, CHLOROFORM-D) δ ppm 1.04 (s, 3H) 1.24 (t, 3H) 1.30-1.50 (m, 4H) 1.65 (d, J=11.72 Hz, 1H) 1.70-1.90 (m, 5H) 1.96 (d, J=9.37 Hz, 1H) 2.30 (d, J=8.20 Hz, 2H) 2.40 (t, J=11.33 Hz, 1H) 2.68 (br. s, 1H) 2.81 (d, J=9.37 Hz, 1H) 2.93-3.08 (m, 2H) 3.18 (t, J=9.77 Hz, 1H) 3.27-3.42 (m, 2H)

3.45 (d, J=10.16 Hz, 1H) 3.52 (t, J=9.77 Hz, 1H) 3.55-3.64 (m, 1H) 3.73 (br, s, 1H) 4.12 (q, J=6.51 Hz, 2H) 4.55 (br, s, 1H). HRMS calculated for C20H35N4O3 [M+H]+ 379.27037, found 379.27102.

Diastereomer 2 (Example 22) (0.485 g, 86%), Retention time: 3.94 minutes (Supercritical fluid chromatography, AD chiral column, column temperature 35° C., Eluents: 40% EtOH+0.1% dimethylethylamine and CO$_2$ as main eluent). $^1$H NMR (400 MHz, CHLOROFORM-D) δ ppm 1.04 (s, 3H) 1.25 (t, 3H) 1.30-1.50 (m, 4H) 1.61-1.69 (m, 1H) 1.69-1.77 (m, 2H) 1.77-1.87 (m, 4H) 1.96 (d, J=10.16 Hz, 1H) 2.26-2.33 (m, 1H) 2.36 (dt, J=8.30, 2.88 Hz, 1H) 2.39 (d, J=3.52 Hz, 1H) 2.59-2.71 (m, 1H) 2.80-2.89 (m, 1H) 2.94-3.07 (m, 1H) 3.17 (t, J=9.96 Hz, 1H) 3.28-3.42 (m, 1H) 3.45 (d, J=10.16 Hz, 1H) 3.49 (s, 1H) 3.51-3.55 (m, 1H) 3.55-3.63 (m, 1H) 3.67-3.80 (m, 1H) 4.12 (q, J=7.29 Hz, 2H) 4.48 (s, 1H). HRMS calculated for C20H35N4O3 [M+H]+ 379.27037, found 379.27026.

Example 23

Ethyl 3-[4-[(3aS,7aR)-2-oxo-3a,4,5,6,7,7a-hexahydro-3H-indol-1-yl]-1-piperidyl]-3-methyl-pyrrolidine-1-carboxylate (mixture of diastereomers)

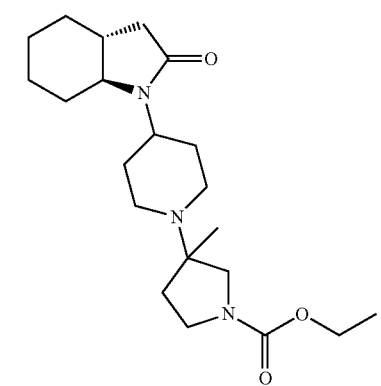

Step A: The preparation of tert-butyl 3-[4-[[(1S,2R)-2-(cyanomethyl)cyclohexyl]amino]-1-piperidyl]-3-methyl-pyrrolidine-1-carboxylate (mixture of diastereomers)

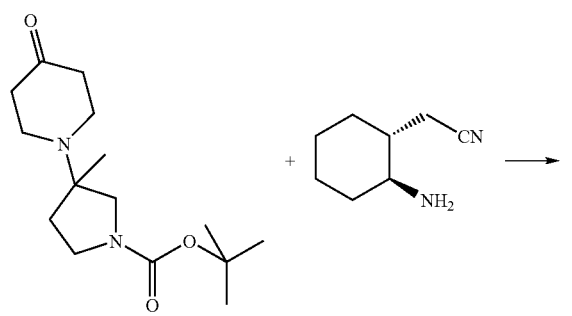

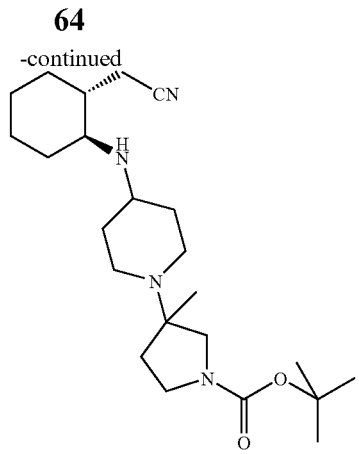

Following the procedure used in step D of the example 14 and starting with 2-[(1R,2S)-2-aminocyclohexyl]acetonitrile (0.342 g, 2.47 mmol) and tert-butyl 3-methyl-3-(4-oxo-1-piperidyl)pyrrolidine-1-carboxylate (0.699 g, 2.47 mmol), the title compound (0.090 g, 8.99%) was obtained after purification by preparative LC/MS (High pH). MS (M+1): 405.23.

Step B: The preparation of 2-[(1R,2S)-2-[[1-(1-tert-butoxycarbonyl-3-methyl-pyrrolidin-3-yl)-4-piperidyl]amino]cyclohexyl]acetic acid (mixture of diastereomers)

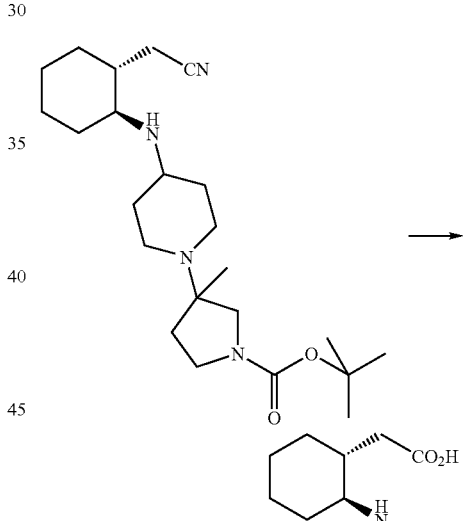

Following the procedure used in step E of the example 14 and starting with tert-butyl 3-[4-[[(1S,2R)-2-(cyanomethyl)cyclohexyl]amino]-1-piperidyl]-3-methyl-pyrrolidine-1-carboxylate (0.090 g, 0.22 mmol), the title compound was obtained. The crude product was used in the subsequent step without any purification.

Step C: The preparation of tert-butyl 3-[4-[(3aR, 7aS)-2-oxo-3a,4,5,6,7,7a-hexahydro-3H-indol-1-yl]-1-piperidyl]-3-methyl-pyrrolidine-1-carboxylate (mixture of diastereomers)

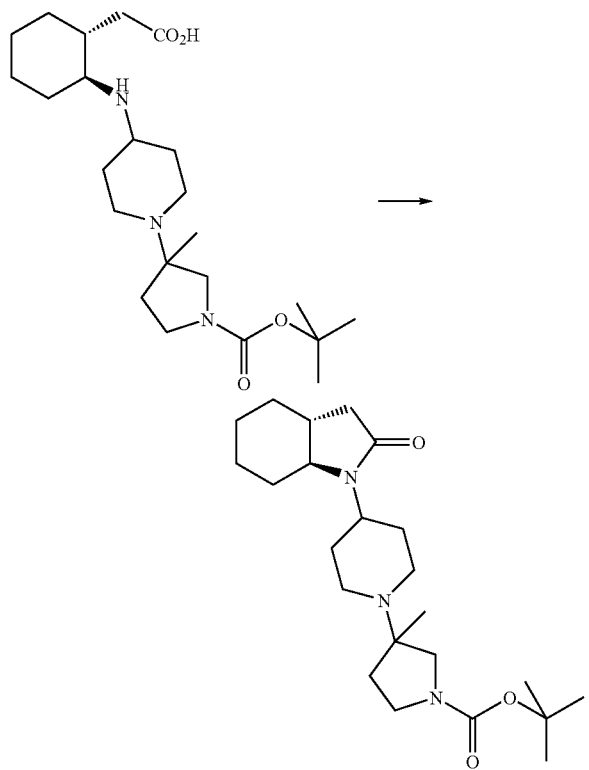

Following the procedure used in step F of the example 14 and starting with 2-[(1R,2S)-2-[[1-(1-tert-butoxycarbonyl-3-methyl-pyrrolidin-3-yl)-4-piperidyl]amino]cyclohexyl]acetic acid (crude from above reaction, 0.094 g, 0.22 mmol), the title compound was obtained. The crude product was used in the subsequent step without any purification. MS (M+1): 406.18.

Step D: The preparation of (3aR,7aS)-1-[1-(3-methylpyrrolidin-3-yl)-4-piperidyl]-3a,4,5,6,7,7a-hexahydro-3H-indol-2-one (mixture of diastereomers)

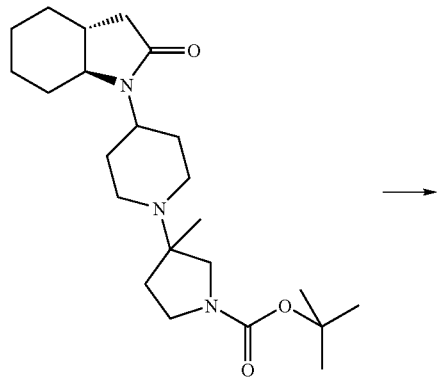

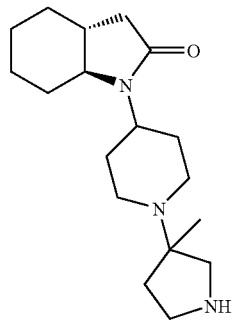

Following the procedure used in step H of the example 14 and starting with tert-butyl 3-[4-[(3aR,7aS)-2-oxo-3a,4,5,6,7,7a-hexahydro-3H-indol-1-yl]-1-piperidyl]-3-methyl-pyrrolidine-1-carboxylate (0.090 g, 0.22 mmol), the title compound was obtained. The crude product was used in the subsequent step without any purification. MS (M+1): 306.16.

Step E: The preparation of ethyl 3-[4-[(3aR,7aS)-2-oxo-3a,4,5,6,7,7a-hexahydro-3H-indol-1-yl]-1-piperidyl]-3-methyl-pyrrolidine-1-carboxylate (mixture of diastereomers)

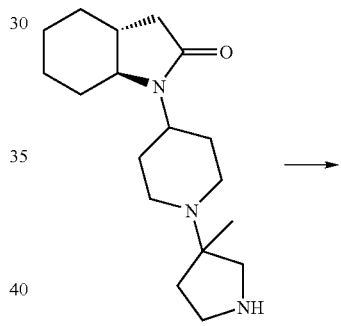

Following the procedure used in step D of the example 12 and starting with (3aR,7aS)-1-[1-(3-methylpyrrolidin-3-yl)-4-piperidyl]-3a,4,5,6,7,7a-hexahydro-3H-indol-2-one (HCl salt, 0.076 g, 0.22 mmol), the title compound (0.025 g, 29.8%) was obtained after purification by preparative LC/MS (High pH). $^1$H NMR (400 MHz, CHLOROFORM-D) δ ppm 1.15-1.25 (m, 5H) 1.26-1.34 (m, 3H) 1.37 (br, s, 3H) 1.58-

1.69 (m, 1H) 1.72 (d, J=7.03 Hz, 1H) 1.75-1.88 (m, 4H) 1.89-2.05 (m, 2H) 2.27 (br, s, 1H) 2.37 (dd, J=16.02, 7.03 Hz, 1H) 2.46 (d, J=10.55 Hz, 1H) 2.54-2.79 (m, 1H) 2.87-3.08 (m, 2H) 3.26-3.46 (m, 2H) 3.46-3.58 (m, 2H) 3.58-3.71 (m, 1H) 3.73-3.89 (m, 1H) 4.03-4.16 (m, 2H) 4.31 (t, J=11.91 Hz, 2H). HRMS calculated for C21H36N3O3 [M+H]+ 378.27512, found 378.27474.

What is claimed is:
1. Propan-2-yl 4-[4-[(3aS,7aS)-2-oxo-3a,4,5,6,7,7a-hexahydro-3H-benzoimidazol-1-yl]-1-piperidyl]-4-methyl-piperidine-1-carboxylate or a pharmaceutically acceptable salt thereof.

* * * * *